US010239239B2

(12) United States Patent
Okazaki et al.

(10) Patent No.: US 10,239,239 B2
(45) Date of Patent: Mar. 26, 2019

(54) INTERNAL RELEASE AGENT, COMPOSITION INCLUDING INTERNAL RELEASE AGENT, AND PROCESS FOR PRODUCING A PLASTIC LENS USING SAME COMPOSITION

(71) Applicant: MITSUI CHEMICALS, INC., Minato-ku, Tokyo (JP)

(72) Inventors: Kouju Okazaki, Omuta (JP); Naoyuki Kakinuma, Ichihara (JP); Motoharu Oiki, Omuta (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 0 days.

(21) Appl. No.: 15/539,911

(22) PCT Filed: Dec. 25, 2015

(86) PCT No.: PCT/JP2015/086334
§ 371 (c)(1),
(2) Date: Jun. 26, 2017

(87) PCT Pub. No.: WO2016/104744
PCT Pub. Date: Jun. 30, 2016

(65) Prior Publication Data

US 2017/0355106 A1 Dec. 14, 2017

(30) Foreign Application Priority Data

Dec. 26, 2014 (JP) ................................ 2014-265858

(51) Int. Cl.

| | |
|---|---|
| ***B29C 39/02*** | (2006.01) |
| ***C08F 2/44*** | (2006.01) |
| ***C08K 5/521*** | (2006.01) |
| ***C08G 75/02*** | (2016.01) |
| ***C08L 75/04*** | (2006.01) |
| ***C08L 101/00*** | (2006.01) |
| ***G02B 1/04*** | (2006.01) |
| ***G02B 3/00*** | (2006.01) |
| ***B29C 33/60*** | (2006.01) |
| ***C08G 18/38*** | (2006.01) |
| ***C07F 9/09*** | (2006.01) |

(52) U.S. Cl.
CPC .............. *B29C 39/02* (2013.01); *B29C 33/60* (2013.01); *C07F 9/091* (2013.01); *C08F 2/44* (2013.01); *C08G 18/3876* (2013.01); *C08G 75/02* (2013.01); *C08K 5/521* (2013.01); *C08L 75/04* (2013.01); *C08L 101/00* (2013.01); *G02B 1/04* (2013.01); *G02B 1/041* (2013.01); *G02B 3/00* (2013.01); *C08G 2125/00* (2013.01); *C08L 2666/40* (2013.01)

(58) Field of Classification Search
CPC ......... B29C 39/02; B29C 33/60; C07F 9/091; C08F 2/44; C08G 18/3876; C08G 75/02; C08G 2125/00; C08K 5/521; C08L 75/04; C08L 101/00; C08L 2666/40; G02B 1/04; G02B 1/041; G02B 3/00
USPC .......................................................... 524/145
See application file for complete search history.

(56) References Cited

U.S. PATENT DOCUMENTS

| | | | | |
|---|---|---|---|---|
| 3,666,843 A * | 5/1972 | Fearing | C07F 9/091 510/467 |
| 4,389,259 A * | 6/1983 | Danner | C07F 9/14 106/14.12 |
| 4,975,328 A | 12/1990 | Hirose et al. | |
| 5,389,708 A | 2/1995 | Kusumoto et al. | |
| 6,852,773 B2 | 2/2005 | Tanabe et al. | |
| 8,022,163 B2 | 9/2011 | Iwazumi et al. | |
| 8,434,866 B2 | 5/2013 | Hayashi et al. | |

(Continued)

FOREIGN PATENT DOCUMENTS

| | | |
|---|---|---|
| EP | 2 757 115 A1 | 7/2014 |
| JP | H 03-281312 A | 12/1991 |

(Continued)

OTHER PUBLICATIONS

International Search Report (PCT/ISA/210) mailed on PCT/JP2015/086334, by the Japanese Patent Office as the International Searching Authority for International Application No. PCT/JP2015/086334.

(Continued)

*Primary Examiner* — Hui H Chin
(74) *Attorney, Agent, or Firm* — Buchanan, Ingersoll & Rooney PC

(57) ABSTRACT

An internal release agent includes at least one phosphodiester represented by the following general formula (1).

(1)

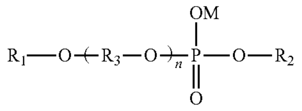

In the formula, $R_1$ and $R_2$ independently represent a hydrocarbon group having 1 to 30 carbon atoms, which is optionally substituted with at least one hydroxyl group, and $R_3$ represents an alkylene group having 2 to 4 carbon atoms. A plurality of $R_3$'s may be the same as or different from each other. M represents a hydrogen atom, an ammonium ion, an alkali metal ion, or a monovalent/divalent alkali earth metal ion, and n is an integer of 1 to 60.

10 Claims, 5 Drawing Sheets

(56) References Cited

U.S. PATENT DOCUMENTS

| | | | |
|---|---|---|---|
| 9,138,775 | B2 | 9/2015 | Otani et al. |
| 2004/0059013 | A1 | 3/2004 | Tanabe et al. |
| 2010/0075154 | A1 | 3/2010 | Hayashi et al. |
| 2010/0234498 | A1 | 9/2010 | Iwazumi et al. |
| 2014/0077418 | A1 | 3/2014 | Otani et al. |

FOREIGN PATENT DOCUMENTS

| | | | |
|---|---|---|---|
| JP | H 03-287641 | A | 12/1991 |
| JP | H 04-134088 | A | 5/1992 |
| JP | H 05-306320 | A | 11/1993 |
| JP | H 06-134773 | A | 5/1994 |
| JP | H 06-136086 | A | 5/1994 |
| JP | H 09-099441 | A | 4/1997 |
| JP | 2000-191673 | A | 7/2000 |
| JP | 2000-256377 | A | 9/2000 |
| JP | 2000-281687 | A | 10/2000 |
| JP | 2001-200022 | A | 7/2001 |
| JP | 2001-300943 | A | 10/2001 |
| JP | 2013-033287 | A | 2/2013 |
| JP | 2013-060488 | A | 4/2013 |
| WO | 02/26875 | A1 | 4/2002 |
| WO | WO 2007/105355 | A1 | 9/2007 |
| WO | WO 2010/032365 | A1 | 3/2010 |
| WO | 2014/130312 | A1 | 8/2014 |

OTHER PUBLICATIONS

Written Opinion (PCT/ISA/237) mailed on PCT/JP2015/086334, by the Japanese Patent Office as the International Searching Authority for International Application No. PCT/JP2015/086334.

Search Report issued by the European Patent Office in corresponding European Patent Application No. 15873312.1-1014 dated Jan. 19, 2018 (4 pages).

* cited by examiner

INTERNAL RELEASE AGENT, COMPOSITION INCLUDING INTERNAL RELEASE AGENT, AND PROCESS FOR PRODUCING A PLASTIC LENS USING SAME COMPOSITION

TECHNICAL FIELD

The present invention relates to an internal release agent used as an additive in cast polymerization, a composition including the internal release agent, and a process for producing a plastic lens using the composition.

BACKGROUND ART

In the related art, many plastic lenses are produced by a cast polymerization method comprising: injecting a composition including a polymerization reactive compound into a cavity in a mold comprised of a glass mold and a tape or a resin gasket, and performing polymerizing and curing by heating or emitting radiation. Typically, since a cured resin adheres to the glass mold and does not release easily, in consideration of productivity, an internal release agent is added to a composition including a polymerization reactive compound, and many proposals on the internal release agent have been made.

As a process for producing a plastic lens using an internal release agent, specifically, a process in which alkoxypolyethylene glycol phosphate is used as an internal release agent is representative (Patent Documents 1, 2, 3, and 4). Furthermore, as a cast polymerization method for obtaining a specific structure whose surface is not smooth, a method of producing a prism lens sheet, a Fresnel lens sheet, or a lenticular lens sheet by adding alkoxypolyethylene glycol phosphate or alkoxypolypropylene glycol phosphate to a monomer having a specific structure has also been proposed (Patent Document 5).

The present inventors of the present invention have been also proposed a method using alkoxypolypropylene glycol phosphate as an internal release agent (Patent Documents 6, 7, and 8), a method using sulfur-containing phosphoric ester (Patent Documents 9, 10, and 11), and a method using a metal catalyst other than tin such as zinc in combination with alkoxypolyethylene glycol phosphoric ester or alkoxypolypropylene glycol phosphoric ester (Patent Document 12).

In addition, a production method of phosphoric ester which is a surfactant has also been disclosed (Patent Document 13).

RELATED DOCUMENT

Patent Document

[Patent Document 1] Japanese Unexamined Patent Publication No. H03-281312

[Patent Document 2] Japanese Unexamined Patent Publication No. 2001-300943

[Patent Document 3] Japanese Unexamined Patent Publication No. H03-287641

[Patent Document 4] Japanese Unexamined Patent Publication No. H09-099441

[Patent Document 5] Japanese Unexamined Patent Publication No. 2001-200022

[Patent Document 6] Japanese Unexamined Patent Publication No. 2000-191673

[Patent Document 7] Japanese Unexamined Patent Publication No. 2000-256377

[Patent Document 8] Japanese Unexamined Patent Publication No. 2000-281687

[Patent Document 9] Japanese Unexamined Patent Publication No. H05-306320

[Patent Document 10] Japanese Unexamined Patent Publication No. H06-134773

[Patent Document 11] Japanese Unexamined Patent Publication No. H06-136086

[Patent Document 12] WO 2007/105355

[Patent Document 13] Japanese Unexamined Patent Publication No. H04-134088

SUMMARY OF THE INVENTION

In a case where a plastic lens is produced by cast polymerization according to the method described in the above-described document, depending on the type of resin, white turbidity sometimes occurs due to the phosphoric ester added as an internal release agent. It is estimated that this is because the phosphoric ester in the related art is likely to form micelles. On the other hand, if the addition amount of the internal release agent is reduced in order to suppress white turbidity of the plastic lens, the releasability is insufficient, and due to this, the glass mold is broken, or cracks may be formed in the resin molded product polymerized and cured in some cases. Therefore, suppression of white turbidity and improvement of releasability are in a trade-off relationship. Thus, a high performance internal release agent which suppresses white turbidity of a plastic lens and has also excellent releasability, a composition including the internal release agent, and a process for producing a plastic lens using the composition have been desired.

That is, an object of the present invention is to provide an internal release agent having superior releasability and transparency than the internal release agents in the related art, a composition including the internal release agent, and a process for producing a plastic lens using the composition.

As a result of intensive studies to solve the above problem, the present inventors found that when a phosphodiester compound having a poly(oxyalkylene)alkyl ether group and an alkyl group (hereinafter, referred to as phosphodiester compound A), represented by the following general formula (1) is used as an internal release agent, even in a case where the phosphodiester compound is added in a large amount, white turbidity is suppressed in the obtained molded product, and high transparency is maintained. That is, they found that by using the phosphodiester compound A represented by the general formula (1), the releasability of the molded product from the mold is excellent, and the transparency of the obtained molded product is also excellent, compared to phosphoric monoester compounds and phosphodiester compounds used in the related art, and completed the present invention.

(1)

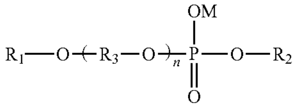

wherein, in the formula, $R_1$ and $R_2$ independently represent a hydrocarbon group having 1 to 30 carbon atoms, which is optionally substituted with at least one hydroxyl group; $R_3$ represents an alkylene group having 2 to 4 carbon atoms, and a plurality of $R_3$'s may be the same as or different from each other; M represents a hydrogen atom, an ammonium ion, an alkali metal ion, or a monovalent/divalent alkali earth metal ion; and n is an integer of 1 to 60.

That is, the present invention can be described as follows.

[1] An internal release agent including at least one phosphodiester compound represented by the following general formula (1):

(1)

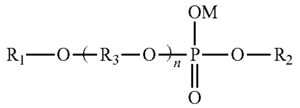

wherein, in the formula, $R_1$ and $R_2$ independently represent a hydrocarbon group having 1 to 30 carbon atoms, which is optionally substituted with at least one hydroxyl group; $R_3$ represents an alkylene group having 2 to 4 carbon atoms and a plurality of $R_3$'s may be the same as or different from each other; M represents a hydrogen atom, an ammonium ion, an alkali metal ion, or a monovalent/divalent alkali earth metal ion; and n is an integer of 1 to 60.

[2] A composition including a polymerization reactive compound and the internal release agent according to [1].

[3] The composition according to [2], in which the amount of the phosphodiester compound represented by the general formula (1) is $1\times10^{-1}$ to $5\times10^{4}$ ppm with respect to the polymerization reactive compound.

[4] The composition according to [2] or [3], in which the polymerization reactive compound is at least one kind of compound selected from group consisting of a polyiso(thio)cyanate compound, a poly(thio)epoxy compound, a polyoxetanyl compound, a polythietanyl compound, a poly(meth)acryloyl compound, a polyalkene compound, an alkyne compound, a poly(thi)ol compound, a polyamine compound, an acid anhydride, and a polycarboxylic acid compound.

[5] A molded product obtained by polymerizing the composition according to any one of [2] to [4].

[6] An optical material comprised of the molded product according to [5].

[7] A plastic lens comprised of the molded product according to [5].

[8] A process for producing a plastic lens including a step of cast-polymerizing the composition according to any one of [2] to [4].

[9] A plastic lens obtained by the production method according to [8].

[10] A phosphodiester compound represented by the following general formula (2):

(2)

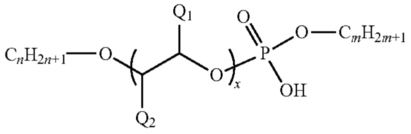

wherein, in the formula (2), x represents an integer of 1 to 23, n represents an integer of 4 to 13; m represents 12 or 13; $Q_1$ and $Q_2$ each represent any of a hydrogen atom and a methyl group, and a plurality of $Q_1$'s and $Q_2$'s may be the same as or different from each other; and a case where both $Q_1$ and $Q_2$ are methyl groups in the repeating unit in parentheses is excluded.

When an internal release agent including the phosphodiester compound A of the present invention is added to the composition and a molded product is produced by polymerization in a mold using this composition, the molded product is easily released from the mold, and thus, productivity is improved, and the production cost can be reduced by reducing mold breakage loss or crack generation in the molded product. Furthermore, the molded product obtained by releasing from the mold has high transparency, and thus, can be suitably used as plastic lenses such as an eyeglass lens, a camera lens, and a pickup lens.

BRIEF DESCRIPTION OF THE DRAWINGS

The above-described objects, other objects, features, and advantages will be made clearer from the preferred embodiments described below, and the following accompanying drawings.

DESCRIPTION OF EMBODIMENTS

Figure 1:
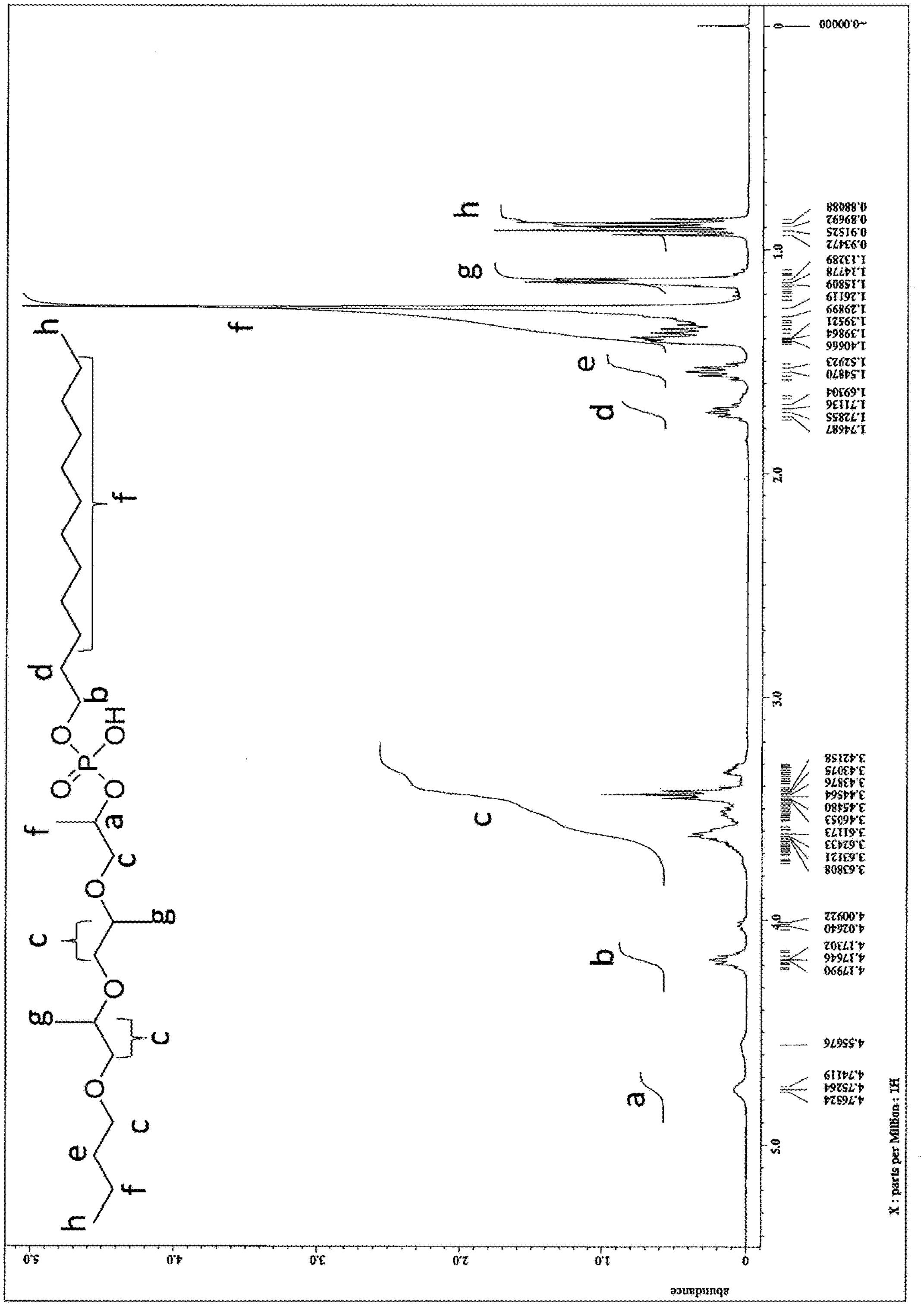
FIG. 1 is a $^{1}$H-NMR spectrum chart of phosphoric ester (110A) including phosphodiester (110) obtained in Production Example 1.

An internal release agent according to the present invention, a composition including the internal release agent, and a process for producing a plastic lens using the composition will be described.

<Internal Release Agent>

The internal release agent of the present invention includes at least one phosphodiester compound A represented by the following general formula (1). In the case of including two or more phosphodiester compounds A, the groups ($R_1$, $R_2$, $R_3$, and M) in the following general formula (1) may be the same or different for each phosphodiester compound A. The phosphodiester compound A may be a mixture of structural isomers.

(1)

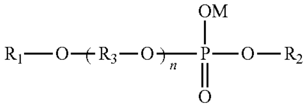

In the formula (1), $R_1$ and $R_2$ independently represent a hydrocarbon group having 1 to 30 carbon atoms which is optionally substituted with at least one hydroxyl group. Examples of the hydrocarbon group having 1 to 30 carbon atoms include an alkyl group having 1 to 30 carbon atoms, an aryl group having 6 to 30 carbon atoms, an alkylaryl group having 7 to 30 carbon atoms, an arylalkyl group having 7 to 30 carbon atoms, and an alkylarylalkyl group having 8 to 30 carbon atoms.

Examples of the alkyl group having 1 to 30 carbon atoms include alkyl groups having 1 to 3 carbon atoms such as a methyl group, an ethyl group, a 1-propyl group, and an isopropyl group, alkyl groups having 4 to 6 carbon atoms such as a 1-butyl group, a 2-butyl group, an isobutyl group, a tert-butyl group, a 1-pentyl group, an isopentyl group, a 2-pentyl group, a 3-pentyl group, a 2-methyl-1-butyl group, a 3-methyl-2-butyl group, a tert-pentyl group, a 1-hexyl group, a 2-methyl-1-pentyl group, a 4-methyl-2-pentyl group, a 2-ethyl-1-butyl group, a cyclopentyl group, a methylcyclopentyl group, a cyclohexyl group, and a methylcyclohexyl group, and alkyl groups having 7 to 30 carbon atoms such as a 1-heptyl group, a 2-heptyl group, a 3-heptyl group, a methylcyclopentylmethyl group, an ethylcyclopentyl group, a cyclopentylethyl group, and a cyclohexylmethyl group.

Examples of the aryl group having 6 to 30 carbon atoms include a phenyl group, a naphthyl group, an anthracenyl group, a phenanthrenyl group, a benzoanthracenyl group, a benzophenanthrenyl group, a naphthacenyl group, a pyrenyl group, a dibenzoanthracenyl group, a pentacenyl group, a picenyl group, and a benzopyrenyl group.

Examples of the alkylaryl group having 7 to 30 carbon atoms include a tolyl group (methylphenyl group), a dimethylphenyl group, a trimethylphenyl group, an ethylphenyl group, a propylphenyl group, a butylphenyl group, a pentylphenyl group, a cyclohexylphenyl group, a trimethylphenyl group, a methylnaphthyl group, a methylphenanthryl group, an ethylphenanthryl group, and a propylphenanthryl group.

Examples of the arylalkyl group having 7 to 30 carbon atoms include a benzyl group, a phenethyl group, a 1-phenylpropyl group, a naphthylmethyl group, and a naphthylethyl group.

Examples of the alkylarylalkyl group having 8 to 30 carbon atoms include a methylbenzyl group, a dimethylbenzyl group, a trimethylbenzyl group, a butylbenzyl group, and a dibutylbenzyl group.

The hydrogen atoms in these hydrocarbon groups may be substituted with one or more hydroxyl groups. Here, $R_1$ and $R_2$ are not limited to these exemplified functional groups.

In the release agent of the present invention, when the number of carbon atoms in the above hydrocarbon group increases, releasability tends to be improved, and when the number of carbon atoms, solubility and dispersibility tend to be lowered. For example, among the hydrocarbon groups having 1 to 30 carbon atoms, a hydrocarbon group having 4 to 30 carbon atoms is relatively preferable, and a hydrocarbon group having 7 to 30 carbon atoms is more preferable. Among the hydrocarbon groups having 1 to 30 carbon atoms, the most preferable form is an alkyl group having 7 to 30 carbon atoms, an alkylaryl group having 7 to 30 carbon atoms, an arylalkyl group having 7 to 30 carbon atoms, or an alkylarylalkyl group having 8 to 30 carbon atoms.

$R_3$ represents an alkylene group having 2 to 4 carbon atoms. In the general formula (1), in a case where a plurality of $R_3$'s are present, the plurality of $R_3$'s may be the same as or different from each other.

Specific examples of $R_3$ include a 1,2-ethylene group, a 1,2-propylene group, a 1,2-butylene group, a 1,3-propylene group, a 1,3-butylene group, and a 1,4-butylene group. Among these, a preferable form is a 1,2-ethylene group or a 1,2-propylene group, and most preferable form is a 1,2-ethylene group.

M represents a hydrogen atom, an ammonium ion, an alkali metal ion, or a monovalent/divalent alkali earth metal ion.

The ammonium ion represents an ammonium ion, a primary ammonium ion, a secondary ammonium ion, a tertiary ammonium ion, or a quaternary ammonium ion, and a functional group other than an ammonium group may be included. Preferable examples of the ammonium ion include an ammonium ion, a methyl ammonium ion, a dimethyl ammonium ion, a trimethyl ammonium ion, a tetramethyl ammonium ion, an ethyl ammonium ion, a diethyl ammonium ion, a triethyl ammonium ion, a 1-propylammonium ion, an isopropylammonium ion, a tris(1-butyl) ammonium ion, a 2-hydroxypropylammonium ion, a bis(2-hydroxyethyl) ammonium ion, a tris(2-hydroxyethyl) ammonium ion, and an ammonium ion of monovalent/divalent bis{N-octyloxy-N-hydro-2,2,6,6-tetramethyl-4-piperazinyl}decanedionic acid ester.

M is preferably a hydrogen atom, an alkali metal ion, or a quaternary ammonium ion, and more preferably an alkali metal ion or a hydrogen atom.

Examples of a preferable alkali metal ion include a lithium ion, a sodium ion, a potassium ion, and a rubidium ion.

n represents an integer of 1 to 60, and is more preferably within a range of 1 to 40, and still more preferably within a range of 1 to 30.

Regarding the above compound (1), representative compounds are exemplified below.

Examples thereof include monomethyl mono-3,6,9-trioxaundecan-1-yl phosphate, sodium monomethyl mono-3,6,9-trioxaundecan-1-yl phosphate, monoethyl mono(14-hydroxy-3,6,9,12-tetraoxatetradecan-1-yl) phosphate, mono(14-hydroxy-3,6,9,12-tetraoxatetradecan-1-yl) monooctyl phosphate, monoethyl mono-3,6,9-trioxahenicosan-1-yl phosphate, monobutyl mono-3,6,9,12,15,18,21-heptaoxatetratriacontan-1-yl phosphate, monobutyl mono-3, 6, 9, 12, 15, 18, 21-hepta oxatetratriacontan-1-yl phosphate, monomethyl mono(23-(nonylphenoxy)-3,6,9,12,15,18,21-heptaoxatricosan-1-yl) phosphate, sodium monomethyl mono(23-(nonylphenoxy)-3,6,9,12,15,18,21-heptaoxatricosan-1-yl) phosphate, monomethyl mono(29-(4-nonylphenoxy)-3,6,9,12,15,18,21,24,27-nonaoxanonacosan-1-yl) phosphate, monoethyl mono(26-(isooctylphenoxy)-3,6,9,12,15,18,21,24-octaoxahexacosan-1-yl) phosphate, monohexadecyl mono(14-hydroxy-3,6,9,12-tetraoxatetradecan-1-yl) phosphate, and monododecyl mono(17-hydroxy-1,4,7,10-tetramethyl-3,6,9,12,15-pentaoxaheptadecan-1-yl) phosphate.

As the phosphodiester compound A included in the internal release agent of the present invention, a novel compound represented by the following general formula (2) can be preferably used.

(2)

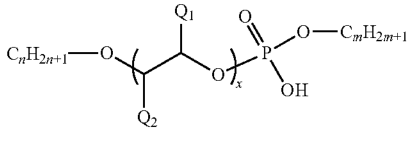

In the formula (2), x represents an integer of 1 to 23, n represents an integer of 4 to 13, and m represents 12 or 13. $Q_1$ and $Q_2$ each represent any of a hydrogen atom and a methyl group, and a plurality of $Q_1$'s and $Q_2$'s may be the same as or different from each other. Here, a case where both $Q_1$ and $Q_2$ are methyl groups in the repeating unit in parentheses is excluded.

As the novel compound represented by the general formula (2), compounds represented by the following general formula (3) or (4) can be preferably used. These compounds can be used as a mixture of structural isomers.

(3)

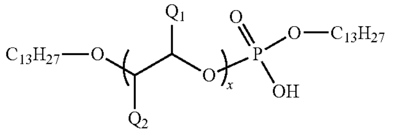

In the general formula (3), x represents an integer of 1 to 23. $Q_1$ and $Q_2$ each represent any of a hydrogen atom and a methyl group, and a plurality of $Q_1$'s and $Q_2$'s may be the same as or different from each other. Here, a case where both $Q_1$ and $Q_2$ are methyl groups in the repeating unit in parentheses is excluded.

First, the production route performed in the order of the step (A)→the step (B)→the step (C) will be described.

The number of the compound in the description below corresponds to the number of the compound in the above reaction formula.

Step (A):

Phosphorus oxyhalide (a) is reacted with polyalkylene glycol monoalkyl ether (b). Polyalkylene glycol monoalkyl ether is added in an amount of 0.1 to 2 equivalents, and preferably 0.8 to 1.2 equivalents with respect to phosphorus oxyhalide, and these compounds are reacted at −60° C. to 100° C., and preferably −40° C. to 50° C. for 1 to 36 hours. By this step, a reaction mixture including the compound (c) is obtained.

(4)

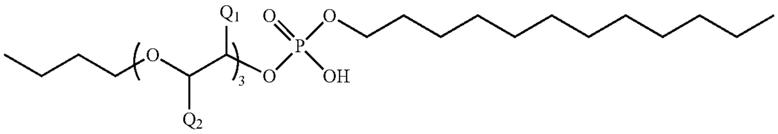

In the general formula (4), $Q_1$ and $Q_2$ each represent any of a hydrogen atom and a methyl group, and a plurality of $Q_1$'s and $Q_2$'s may be the same as or different from each other. Here, the case where both $Q_1$ and $Q_2$ are hydrogen atoms and the case where both are methyl groups, in the repeating unit in parenthesis, are excluded.

The compound represented by the general formula (1) of the present invention is synthesized by a known production method. For example, representative compounds represented by the following general formula (h), selected from the compounds represented by the general formula (1) are exemplified, and the main production route is shown in the following reaction formula.

At this time, for the purpose of improving the reaction rate, a tertiary amine such as triethylamine or pyridine may be added. The addition amount of the tertiary amine is 0.1 to 4.0 equivalents, and preferably 1.8 to 2.2 equivalents, with respect to the phosphorus oxyhalide. Examples of the phosphorus oxyhalide include phosphorus oxychloride and phosphorus oxybromide, and among these, phosphorus oxychloride is preferable.

Step (B):

An alcohol (d) (an alcohol having no alkyleneoxy structure) other than the compound (b) is added to the reaction mixture including the compound (c) obtained in the step (A). The alcohol (d) is added in an amount of 0.1 to 2 equivalents,

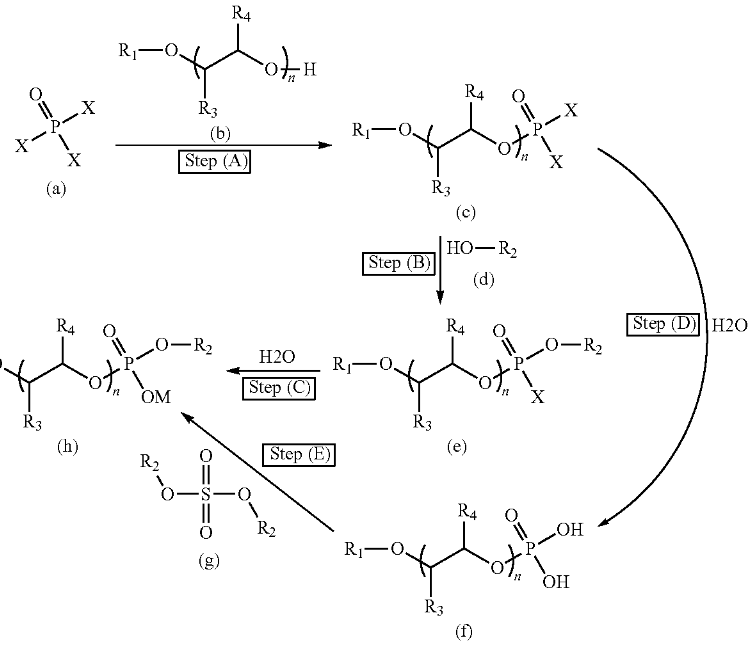

X: halogent atom
R1: the same meaning as in general formula (1)
R2: the same meaning as in general formula (1)
R3, R4: H, Me
n: the same meaning as in general formula (1)

and preferably 0.8 to 1.2 equivalents with respect to phosphorus oxyhalide, and these compounds are reacted at −60° C. to 100° C., and preferably −40° C. to 50° C. for 1 to 36 hours. By this step, a reaction mixture including phosphoric diester monohalide (e) is obtained.

Step (C):

After the reaction, 1 to 2 equivalents of water with respect to phosphorus oxyhalide is added to the reaction mixture obtained in the step (B), and the phosphoric acid diester monohalide (e) is hydrolyzing to obtain phosphodiester (h). At this time, bases and acids such as sodium hydroxide, potassium hydroxide, sodium hydrogen carbonate, sodium bicarbonate, potassium carbonate, potassium hydrogen carbonate, sodium phosphate, sodium acetate, ammonia, acetic acid, hydrochloric acid, and sulfuric acid may be added. The reaction temperature is 0° C. to 100° C., and preferably 10° C. to 50° C. The liquid property of the solution is preferably pH 8 or less, and more preferably pH 7 or less.

A solvent may be added in the reactions of the steps (A) to (C) according to the properties of the raw materials, the intermediates, the final desired products. Examples thereof include acetic ester compounds such as butyl acetate, ketone compounds such as acetone, ether compounds such as diethyl ether and tetrahydrofuran, nitrile compounds such as acetonitrile, aprotic polar compounds such as N,N-dimethylformamide, halogen compounds such as chloroform and chlorobenzene, and hydrocarbon compounds such as hexane and toluene.

Next, the production route performed in the order of the step (A)→the step (D)→the step (E) will be described.

Since the step (A) can be carried out in the same manner as described above, the explanation is not repeated.

Step (D):

Water is added to the compound (c) obtained in the step (A), and hydrolysis is carried out in the same manner as in the step (C), whereby a phosphoric monoester body (f) is obtained.

Step (E):

The dialkyl sulfate (g) is added to the phosphoric monoester form (f) obtained in the step (D), and esterification of the hydroxyl group bonded to the phosphorus atom was performed, whereby a target compound (compound (h)) is obtained. At this time, for the purpose of improving the reaction rate and selectivity, a method in which one of the two hydroxyl groups bonded to the phosphorus atom is neutralized with a base is preferably used. The base to be used is not particularly limited, and an alkali metal such as sodium hydroxide, sodium carbonate, sodium hydrogencarbonate, or potassium hydroxide is preferably used.

The reaction solvent used in the reaction of the steps (A) to (E) is suitably selected according to the properties of the raw materials, the intermediates, the final desired products. Examples thereof include water, alcohol compounds such as methanol, acetic ester compounds such as butyl acetate, ketone compounds such as acetone, ether compounds such as THF (tetrahydrofuran), nitrile compounds such as acetonitrile, aprotic polar compounds such as N,N-dimethylformamide, halogen compounds such as chloroform and chlorobenzene, and hydrocarbon compounds such as hexane and toluene.

In the present invention, one or a mixture of two or more selected from the phosphodiester compounds A represented by the general formula (1) are used as an internal release agent.

The specific effects generated by the structure represented by the general formula (1) will be described with reference to a typical compound. For example, the phosphodiester compound A of alkoxypolyalkylene glycol and alkyl alcohol which is the phosphodiester compound of the present invention tends to be less likely to form micelles and has also good dispersibility, and thus, exhibits high transparency and excellent releasability, compared to a phosphodiester compound (a structure in which two same alkyl ether groups are bonded to the P atom) with alkyl alcohol and a phosphoric monoester compound with alkyl alcohol. In the same manner, even compared to a phosphodiester compound (a structure in which two same poly(oxyalkylene) alkyl ether groups are bonded to the P atom) of alkoxypolyalkylene glycol and a phosphoric monoester compound of alkoxyalkylene glycol, the phosphodiester compound A exhibits better releasability while maintaining high transparency. That is, since the phosphodiester compound A of the present invention is superior in releasability and transparency to those of phosphodiester compounds or phosphoric monoester compounds which have been used in the related art, the phosphodiester compound A is extremely useful as an internal release agent.

In the internal release agent of the present invention, compounds other than the phosphodiester compound A represented by the general formula (1) may be included within a range not impairing the effects of the present invention. Examples of the compounds other than the compound of the general formula (1) include a phosphodiester compound B which is a by-product, a phosphoric monoester compound C derived from an intermediate, and alcohol D, represented by the following general formula.

Phosphodiester compound B

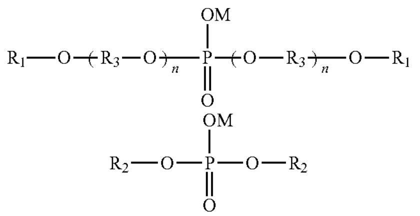

Phosphoric monoester compound C

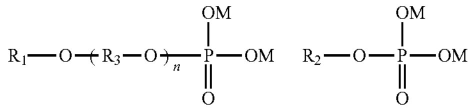

Alcohol D

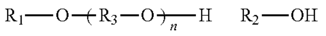

In the formula, $R_1$, $R_2$, $R_3$, M, and n have the same meaning as those in the general formula (1).

Furthermore, as other components, phosphoric acid derived from raw materials, a reaction solvent, and the like can be included.

The phosphodiester compound A represented by the general formula (1) is included in a range of 0.1 to 100% by weight, preferably in a range of 1 to 100% by weight, and more preferably in a range of 5 to 100% by weight, in the internal release agent (100% by weight) of the present invention. When the purity of the phosphodiester compound A represented by the general formula (1) is within the above-described ranges, releasability is excellent, and thus, it is preferable.

In a case where the compounds B to D of the general formula are included in addition to the phosphodiester compound A of the general formula (1), the allowable content of the compounds B to D is in a range of 0.1 to 99.9% by weight, preferably in a range of 1 to 99% by weight, and more preferably in a range of 5 to 95% by weight, in the total of 100% by weight of the compounds A to D. If the content of the compounds B to D other than the phosphodiester compound A represented by the general formula (1) is within the above-described ranges, releasability is excellent, and thus, it is preferable.

The internal release agent of the present invention can include compounds B to D other than the phosphodiester compound A represented by the following general formula (1). In this case, the phosphodiester compound A can be included in an amount of 0.1 to 99.9% by weight, preferably 1 to 99% by weight, more preferably 5 to 95% by weight, and particularly preferably 5 to 80% by weight, the phosphodiester compound B can be included in an amount of 0 to 99.8% by weight, preferably 0 to 98% by weight, more preferably 0 to 90% by weight, and particularly preferably 5 to 80% by weight, the phosphoric monoester compound C can be included in an amount of 0.05 to 99.85% by weight, preferably 0.5 to 98.5% by weight, more preferably 2.5 to 92.5% by weight, and particularly preferably 5 to 80% by weight, and the alcohol D can be included in an amount of 0.05 to 99.85% by weight, preferably 0.5 to 98.5% by weight, more preferably 2.5 to 92.5% by weight, and particularly preferably 10 to 85% by weight, in the total of 100% by weight of the compounds A to D. These numerical ranges can be combined suitably.

Within the above-described ranges, releasability is excellent, and thus, it is preferable.

The internal release agent including phosphodiester of the present invention can also be used by mixing with other internal release agents.

<Composition>

The composition of the present invention includes a polymerization reactive compound and the internal release agent described above.

The addition amount of the phosphodiester compound A represented by the general formula (1) included in the internal release agent of the present invention varies depending on various compounds including a polymerization reactive compound and the shape of a mold, and is in a range of $1\times10^{-1}$ ppm to $5\times10^{4}$ ppm, preferably in a range of 1 ppm to $2\times10^{4}$ ppm, and more preferably in a range of 5 ppm to $1\times10^{4}$ ppm with respect to the polymerization reactive compound.

By including the phosphodiester compound A represented by the general formula (1) within the above-described range, it is possible to obtain a molded product having excellent releasability and excellent transparency.

In the polymerization reactive compound included in the composition of the present invention, even in the presence or absence of the additives such as an initiator and a catalyst added as necessary, a polymerization reactive compound having at least one or more polymerizable functional groups which are capable of being self-polymerized, copolymerized, or addition-polymerized is included.

More specific examples of the compound having a polymerizable functional group capable of self-polymerization, copolymerization, or addition polymerization include a polyiso(thio)cyanate compound having two or more arbitrarily selected from isocyanato groups and isothiocyanato groups, a poly(thio)epoxy compound having two or more arbitrarily selected from epoxy groups and thioepoxy groups, a polyoxetanyl compound having two or more oxetanyl groups, a polythietanyl compound having two or more thietanyl groups or having an oxetanyl group and a thietanyl group, a poly(meth)acryloyl compound having two or more arbitrarily selected from a methacryloyloxy group, an acryloyloxy group, a methacryloylthio group, an acryloylthio group, a methacrylamide group, and an acrylamide group, a polyalkene compound having two or more polymerizable carbon-carbon double bond groups other than a methacryloyloxy group, an acryloyloxy group, a methacryloylthio group, an acryloylthio group, a methacrylamide group, and an acrylamide group, an alkyne compound having one or more polymerizable carbon-carbon triple bond groups, a poly(thi)ol compound having two or more arbitrarily selected from a hydroxy group and a mercapto group (here, the alcohol used as a solvent is not included), a polyamine compound having two or more arbitrarily selected from amino groups and secondary amino groups, an acid anhydride having one or more acid anhydride groups, and a polycarboxylic acid compound having two or more carboxyl groups.

Examples of the polyiso(thio)cyanate compound include aliphatic polyisocyanate compounds such as tetramethylene diisocyanate, pentamethylene diisocyanate, hexamethylene diisocyanate, pentamethylene diisocyanate, octamethylene diisocyanate, 2,2,4-trimethylhexamethylene diisocyanate, 2,4,4-trimethylhexamethylene diisocyanate, lysinediisocyanato methyl ester, lysine triisocyanate, and xylylene diisocyanate;

alicyclic polyisocyanate compounds such as isophorone diisocyanate, bis(isocyanatomethyl) cyclohexane, dicyclohexylmethane diisocyanate, dicyclohexyldimethylmethane isocyanate, 2,5-bis(isocyanatomethyl)bicyclo-[2.2.1]-heptane, 2,6-bis(isocyanatomethyl)bicyclo-[2.2.1]-heptane, 3,8-bis(isocyanatomethyl) tricyclodecane, 3,9-bis(isocyanatomethyl) tricyclodecane, 4,8-bis(isocyanatomethyl) ticyclodecane, and 4,9-bis(isocyanatomethyl) tricyclodecane;

aromatic polyisocyanate compounds such as tolylene diisocyanate, 4,4'-diphenylmethane diisocyanate, diphenylsulfide-4,4-diisocyanate, and phenylene diisocyanate;

heterocyclic polyisocyanate compounds such as 2,5-diisocyanatothiophene, 2,5-bis(isocyanatomethyl) thiophene, 2,5-diisocyanatotetrahydrothiophene, 2,5-bis(isocyanatomethyl) tetrahydrothiophene, 3,4-bis(isocyanatomethyl) tetrahydrothiophene, 2,5-diisocyanato-1,4-dithiane, 2,5-bis(isocyanatomethyl)-1,4-dithiane, 4,5-diisocyanato-1,3-dithiolane, and 4,5-bis(isocyanatomethyl)-1,3-dithiolane.

aliphatic polyisothiocyanate compounds such as hexamethylene diisothiocyanate, lysine diisothiocyanate methyl ester, lysine triisothiocyanate, m-xylylene diisothiocyanate, bis(isothiocyanatomethyl) sulfide, bis(isothiocyanatoethyl) sulfide, and bis(isothiocyanatoethyl) disulfide;

alicyclic polyisothiocyanate compounds such as isophorone diisothiocyanate, bis(isothiocyanatomethyl)cyclohexane, dicyclohexylmethane diisothiocyanate, cyclohexane diisothiocyanate, methylcyclohexane diisothiocyanate, 2,5-bis(isothiocyanatomethyl)bicyclo-[2.2.1]-heptane, 2,6-bis(isothiocyanatomethyl)bicyclo-[2.2.1]-heptane, 3,8-bis(isothiocyanatomethyl)tricyclodecane, 3,9-bis(isothiocyanatomethyl)tricyclodecane, 4,8-bis(isothiocyanatomethyl)ticyclodecane, and 4,9-bis(isothiocyanatomethyl)tricyclodecane;

aromatic polyisothiocyanate compounds such as tolylene diisothiocyanate, 4,4-diphenylmethane diisothiocyanate, and diphenyldisulfide-4,4-diisothiocyanate; and sulfur-containing heterocyclic polyisothiocyanate compounds such as 2,5-diisothiocyanatothiophene, 2,5-bis(isothiocyanatomethyl)thiophene, 2,5-isothiocyanatotetrahydrothiophene, 2,5-bis(isothiocyanatomethyl) tetrahydrothiophene, 3,4-bis(isothiocyanatomethyl)

tetrahydrothiophene, 2,5-diisothiocyanato-1,4-dithiane, 2,5-bis(isothiocyanatomethyl)-1,4-dithiane, 4,5-diisothiocyanato-1,3-dithiolane, and 4,5-bis(isothiocyanatomethyl)-1,3-dithiolane.

Examples of the poly(thio)epoxy compound include poly-epoxy compounds such as bisphenol A diglycidyl ether;

linear aliphatic 2,3-epoxypropylthio compounds such as bis(2,3-epoxypropyl) sulfide, bis(2,3-epoxypropyl) disulfide, bis(2,3-epoxypropylthio) methane, 1,2-bis(2,3-epoxypropyl) thioethane, 1,2-bis(2,3-epoxypropylthio) propane, 1,3-bis(2,3-epoxypropylthio) propane, 1,3-bis(2,3-epoxypropylthio)-2-methyl propane, 1,4-bis(2,3-epoxypropylthio) butane, 1,4-bis(2,3-epoxypropylthio)-2-methyl butane, 1,3-bis(2,3-epoxypropylthio) butane, 1,5-bis(2,3-epoxypropylthio) pentane, 1,5-bis(2,3-epoxypropylthio)-2-methyl pentane, 1,5-bis(2,3-epoxypropylthio)-3-thiapentane, 1,6-bis(2,3-epoxypropylthio) hexane, 1,6-bis(2,3-epoxypropylthio)-2-methyl hexane, 3,8-bis(2,3-epoxypropylthio)-3,6-dithiaoctane, 1,2,3-tris(2,3-epoxypropylthio) propane, 2,2-bis(2,3-epoxypropylthio)-1,3-bis(2,3-epoxypropylthiomethyl) propane, 2,2-bis(2,3-epoxypropylthiomethyl)-1-(2,3-epoxypropylthio) butane, 1,5-bis(2,3-epoxypropylthio)-2-(2,3-epoxypropylthiomethyl)-3-thiapentane, 1,5-bis(2,3-epoxypropylthio)-2,4-bis(2,3-epoxypropylthiomethyl)-3-thiapentane, 1-(2,3-epoxypropylthio)-2,2-bis(2,3-epoxypropylthiomethyl)-4-thiahexane, 1,5,6-tris(2,3-epoxypropylthio)-4-(2,3-epoxypropylthiomethyl)-3-thiahexane, 1,8-bis(2,3-epoxypropylthio)-4-(2,3-epoxypropylthiomethyl)-3,6-dithiaoctane, 1,8-bis(2,3-epoxypropylthio)-4,5-bis(2,3-epoxypropylthiomethyl)-3,6-dithiaoctane, 1,8-bis(2,3-epoxypropylthio)-4,4-bis(2,3-epoxypropylthiomethyl)-3,6-dithiaoctane, 1,8-bis(2,3-epoxypropylthio)-2,5-bis(2,3-epoxypropylthiomethyl)-3,6-dithiaoctane, 1,8-bis(2,3-epoxypropylthio)-2,4,5-tris(2,3-epoxypropylthiomethyl)-3,6-dithiaoctane, 1,1,1-tris[[2-(2,3-epoxypropylthio)ethyl]thiomethyl]-2-(2,3-epoxypropylthio)ethane, 1,1,2,2-tetrakis[[2-(2,3-epoxypropylthio)ethyl]thiomethyl]ethane, 1,11-bis(2,3-epoxypropylthio)-4,8-bis(2,3-epoxypropylthiomethyl)-3,6,9-trithiaundecane, 1,11-bis(2,3-epoxypropylthio)-4,7-bis(2,3-epoxypropylthiomethyl)-3,6,9-trithiaundecane, and 1,11-bis(2,3-epoxypropylthio)-5,7-bis(2,3-epoxypropylthiomethyl)-3,6,9-trithiaundecane;

cyclic aliphatic 2,3-epoxypropylthio compounds such as 1,3-bis(2,3-epoxypropylthio) cyclohexane, 1,4-bis(2,3-epoxypropylthio) cyclohexane, 1,3-bis(2,3-epoxypropylthiomethyl) cyclohexane, 1,4-bis(2,3-epoxypropylthiomethyl) cyclohexane, 2,5-bis(2,3-epoxypropylthiomethyl)-1,4-dithiane, 2,5-bis[[2-(2,3-epoxypropylthio)ethyl]thiomethyl]-1,4-dithiane, and 2,5-bis(2,3-epoxypropylthiomethyl)-2,5-dimethyl-1,4-dithiane; and aromatic 2,3-epoxypropylthio compounds such as 1,2-bis(2,3-epoxypropylthio) benzene, 1,3-bis(2,3-epoxypropylthio) benzene, 1,4-bis(2,3-epoxypropylthio) benzene, 1,2-bis(2,3-epoxypropylthiomethyl) benzene, 1,3-bis(2,3-epoxypropylthiomethyl) benzene, 1,4-bis(2,3-epoxypropylthiomethyl) benzene, bis[4-(2,3-epoxypropylthio)phenyl] methane, 2,2-bis[4-(2,3-epoxypropylthio)phenyl] propane, bis[4-(2,3-epoxypropylthio)phenyl] sulfide, bis[4-(2,3-epoxypropylthio)phenyl] sulfone, and 4,4'-bis(2,3-epoxypropylthio) biphenyl.

Examples of the polyoxetanyl compound include 3-ethyl-3-hydroxymethyl oxetane, 1,4-bis{[(3-ethyl-3-oxetanyl)methoxy]methyl} benzene, 3-ethyl-3-(phenoxymethyl) oxetane, di[1-ethyl-(3-oxetanyl)]methyl ether, 3-ethyl-3-(2-ethylhexyloxymethyl) oxetane, and phenol novolac oxetane.

Examples of the polythietanyl compound include 1-{4-(6-mercaptomethylthio)-1,3-dithianylthio}-3-{2-(1,3-dithietanyl)}methyl-7,9-bis(mercaptomethylthio) 2,4,6,10-tetrathiaundecane, 1,5-bis{4-(6-mercaptomethylthio)-1,3-dithianylthio}-3-{2-(1,3-dithietanyl)}methyl-2,4-dithiapentane, 4,6-bis[3-{2-(1,3-dithietanyl)}methyl-5-mercapto-2,4-dithiapentylthio]-1,3-dithiane, 3-{2-(1,3-dithietanyl)}methyl-7,9-bis(mercaptomethylthio)-1,11-dimercapto-2,4,6,10-tetrathiaundecane, 9-{2-(1,3-dithietanyl)}methyl-3,5,13,15-tetrakis(mercaptomethylthio)-1,17-dimercapto-2,6,8,10,12,16-hexathiaheptadecane, 3-{2-(1,3-dithietanyl)}methyl-7,9,13,15-tetrakis(mercaptomethylthio)-1,17-dimercapto-2,4,6,10,12,16-hexathiaheptadecane, 3,7-bis{2-(1,3-dithietanyl)}methyl-1,9-dimercapto-2,4,6,8-tetrathianonane, 4,5-bis[1-{2-(1,3-dithietanyl)}-3-mercapto-2-thiapropylthio]-1,3-dithiolane, 4-[1-{2-(1,3-dithietanyl)}-3-mercapto-2-thiapropylthio]-5-{1,2-bis(mercaptomethylthio)-4-mercapto-3-thiabutylthio}-1,3-dithiolane, and 4-{4-(5-mercaptomethylthio-1,3-dithiolanyl)thio}-5-[1-{2-(1,3-dithietanyl)}-3-mercapto-2-thiapropylthio]-1,3-dithiolane.

Examples of the poly(meth)acryloyl compound include diacryloyl compounds such as ethylene glycol diacrylate, 1,3-butylene glycol diacrylate, 1,4-butanediol diacrylate, 1,6-hexanediol diacrylate, cyclohexanedimethanol diacrylate, alkoxylated hexanediol diacrylate, neopentyl glycol diacrylate, caprolactone modified neopentyl glycol hydroxypivalate diacrylate, cyclohexanedimethanol diacrylate, diethylene glycol diacrylate, dipropylene glycol diacrylate, bisphenol A diacrylate, ethoxylated bisphenol A diacrylate, hydroxypivalaldehyde modified trimethylolpropane diacrylate, neopentyl glycol diacrylate, polyethylene glycol diacrylate, propoxylated neopentyl glycol diacrylate, tetraethylene glycol diacrylate, tricyclodecane dimethanol diacrylate, triethylene glycol diacrylate, and tripropylene glycol diacrylate;

triacryloyl compounds such as glycerol triacrylate, ethoxylated trimethylolpropane triacrylate, pentaerythritol triacrylate, propoxylated glyceryl triacrylate, propoxylated trimethylolpropane triacrylate, and tris(2-hydroxyethyl)isocyanurate triacrylate; and tetraacryloyl compounds such as ditrimethylolpropane tetraacrylate, dipentaerythritol pentaacrylate, ethoxylated pentaerythritol tetraacrylate, pentaerythritol tetraacrylate, and caprolactone-modified dipentaerythritol hexaacrylate.

Examples of the polyalkene compound include polyethylene, polypropylene, polyisobutylene, diethylene glycol bis(allylcarbonate), and divinylbenzene.

Examples of the alkyne compound include hydrocarbon-based alkynes such as 2-butyne, 2-pentyne, 2-hexyne, 3-hexyne, 2-heptyne, 3-heptyne, 2-octyne, 3-octyne, 4-octyne, diisopropyl acetylene, 2-nonyne, 3-nonyne, 4-nonyne, 5-nonyne, 2-decyne, 3-decyne, 4-decyne, 5-decyne, di-tert-butyl acetylene, diphenyl acetylene, dibenzyl acetylene, methyl-iso-propyl acetylene, methyl-tert-butyl acetylene, ethyl-iso-propyl acetylene, ethyl-tert-butyl acetylene, n-propyl-iso-propyl acetylene, n-propyl-tert-butyl acetylene, phenyl methyl acetylene, phenyl ethyl acetylene, phenyl-n-propyl acetylene, phenyl-iso-propyl acetylene, phenyl-n-butyl acetylene, and phenyl-tert-butylacetylene; and alkynyl alcohols such as acetylene diol, propinol, butynol, pentynol, hexynol, hexynediol, heptynol, heptynediol, octynol, and octynediol, and alkynyl amines in which some or all OH groups of the alkynyl alcohols have been substituted with $NH_2$ groups.

Among the poly(thi)ol compounds (here, alcohol used as a solvent is not included), examples of the polyol compound include aliphatic polyols such as ethylene glycol, diethylene glycol, propylene glycol, dipropylene glycol, tripropylene glycol, butylene glycol, neopentyl glycol, glycerin, trimethylol ethane, trimethylol propane, ditrimethylol propane, butanetriol, 1,2-methyl glucoside, pentaerythritol, dipentaerythritol, tripentaerythritol, sorbitol, erythritol, threitol, ribitol, arabinitol, xylitol, allitol, mannitol, dulcitol, iditol, glycol, inositol, hexanetriol, triglycerose, diglylperol, triethylene glycol, polyethylene glycol, tris(2-hydroxyethyl)isocyanurate, cyclobutanediol, cyclopentane diol, cyclohexane diol, cycloheptane diol, cyclooctane diol, cyclohexane dimethanol, hydroxypropyl cyclohexanol, tricyclo[5.2.1.0$^{2,6}$]decane-dimethanol, bicyclo[4.3.0]-nonanediol, dicyclohexanediol, tricyclo[5.3.1.1]dodecanediol, bicyclo[4.3.0]nonanedimethanol, tricyclo[5.3.1.1]dodecane-diethanol, hydroxypropyl tricyclo[5.3.1.1]dodecanol, spiro[3.4]octanediol, butyl cyclohexanediol, 1,1'-bicyclohexylidenediol, cyclohexanetriol, maltitol, and lactose;

aromatic polyols such as dihydroxynaphthalene, trihydroxynaphthalene, tetrahydroxynaphthalene, dihydroxybenzene, benzenetriol, biphenyl tetraol, pyrogallol, (hydroxynaphthyl) pyrogallol, trihydroxyphenanthrene, bisphenol A, bisphenol F, xylylene glycol, di(2-hydroxyethoxy) benzene, bisphenol A-bis-(2-hydroxyethylether), tetrabromobisphenol A, and tetrabromobisphenol A-bis-(2-hydroxyethylether);

halogenated polyols such as dibromoneopentyl glycol; and polymeric polyols such as an epoxy resin. In the present embodiment, at least one selected from these can be used in combination.

In addition, examples of the polyol compound include condensation reaction products of an organic acid such as oxalic acid, glutamic acid, adipic acid, acetic acid, propionic acid, cyclohexanecarboxylic acid, β-oxocyclohexanepropionic acid, dimer acid, phthalic acid, isophthalic acid, salicylic acid, 3-bromopropionic acid, 2-bromoglycol, dicarboxycyclohexane, pyromellitic acid, butanetetracarboxylic acid, or bromophthalic acid with the above-described polyols;

addition reaction products of the above-described polyols with an alkylene oxide such as ethylene oxide or propylene oxide;

addition reaction product of an alkylenepolyamine with an alkylene oxide such as ethylene oxide or propylene oxide;

bis-[4-(hydroxyethoxy)phenyl] sulfide, bis-[4-(2-hydroxypropoxy)phenyl] sulfide, bis-[4-(2,3-dihydroxypropoxy)phenyl] sulfide, bis-[4-(4-hydroxycyclohexyloxy)phenyl] sulfide, bis-[2-methyl-4-(hydroxyethoxy)-6-butylphenyl] sulfide, and compounds obtained by adding three or less molecules on average of ethylene oxide and/or propylene oxide per hydroxyl group to these compounds; and polyols containing a sulfur atom such as di-(2-hydroxyethyl) sulfide, 1,2-bis-(2-hydroxyethylmercapto) ethane, bis(2-hydroxyethyl) disulfide, 1,4-dithiane-2,5-diol, bis(2,3-dihydroxypropyl) sulfide, tetrakis(4-hydroxy-2-thiabutyl) methane, bis(4-hydroxyphenyl) sulfone (bisphenol S), tetrabromobisphenol S, tetramethyl bisphenol S, 4,4'-thiobis(6-tert-butyl-3-methylphenol), and 1,3-bis(2-hydroxyethylthioethyl)-cyclohexane. In the present embodiment, at least one type selected from these can be used in combination.

Examples of the polythiol compound include aliphatic polythiol compounds such as methanedithiol, 1,2-ethanedithiol, 1,2,3-propanetrithiol, 1,2-cyclohexanedithiol, bis(2-mercaptoethyl) ether, tetrakis(mercaptomethyl) methane, diethylene glycol bis(2-mercaptoacetate), diethylene glycol bis(3-mercaptopropionate), ethylene glycol bis(2-mercaptoacetate), ethylene glycol bis(3-mercaptopropionate), trimethylolpropane tris(2-mercaptoacetate), trimethylolpropane tris(3-mercaptopropionate), trimethylolethane tris(2-mercaptoacetate), trimethylolethane tris(3-mercaptopropionate), pentaerythritol tetrakis(2-mercaptoacetate), pentaerythritol tetrakis(3-mercaptopropionate), bis(mercaptomethyl) sulfide, bis(mercaptomethyl) disulfide, bis(mercaptoethyl) sulfide, bis(mercaptoethyl) disulfide, bis(mercaptopropyl) sulfide, bis(mercaptomethylthio)methane, bis(2-mercaptoethylthio) methane, bis(3-mercaptopropylthio) methane, 1,2-bis(mercaptomethylthio) ethane, 1,2-bis(2-mercaptoethylthio) ethane, 1,2-bis(3-mercaptopropylthio) ethane, 1,2,3-tris(mercaptomethylthio) propane, 1,2,3-tris(2-mercaptoethylthio) propane, 1,2,3-tris(3-mercaptopropylthio) propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, tetrakis(mercaptomethylthiomethyl) methane, tetrakis(2-mercaptoethylthiomethyl) methane, tetrakis(3-mercaptopropylthiomethyl) methane, bis(2,3-dimercaptopropyl) sulfide, 2,5-dimercaptomethyl-1,4-dithiane, 2,5-dimercapto-1,4-dithiane, 2,5-dimercaptomethyl-2,5-dimethyl-1,4-dithiane, and esters of these thioglycolic acid and mercaptopropionic acid, hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), 2-mercaptoethyl ether bis(2-mercaptoacetate), 2-mercaptoethyl ether bis(3-mercaptopropionate), thiodiglycolic acid bis(2-mercaptoethylester), thiodipropionic acid bis(2-mercaptoethylester), dithiodiglycolic acid bis(2-mercaptoethyl ester), dithiodipropionic acid bis(2-mercaptoethylester), 1,1,3,3-tetrakis(mercaptomethylthio) propane, 1,1,2,2-tetrakis(mercaptomethylthio) ethane, 4,6-bis(mercaptomethylthio)-1,3-dithiane, tris(mercaptomethylthio) methane, and tris(mercaptoethylthio) methane;

aromatic polythiol compounds such as 1,2-dimercaptobenzene, 1,3-dimercaptobenzene, 1,4-dimercaptobenzene, 1,2-bis(mercaptomethyl) benzene, 1,3-bis(mercaptomethyl) benzene, 1,4-bis(mercaptomethyl) benzene, 1,2-bis(mercaptoethyl) benzene, 1,3-bis(mercaptoethyl) benzene, 1,4-bis(mercaptoethyl) benzene, 1,3,5-trimercaptobenzene, 1,3,5-tris(mercaptomethyl) benzene, 1,3,5-tris(mercaptomethyleneoxy) benzene, 1,3,5-tris(mercaptoethyleneoxy) benzene, 2,5-toluenedithiol, 3,4-toluenedithiol, 1,5-naphthalenedithiol, and 2,6-naphthalenedithiol; and heterocyclic polythiol compounds such as 2-methylamino-4,6-dithiol-sym-triazine, 3,4-thiophene dithiol, bismuthiol, 4,6-bis(mercaptomethylthio)-1,3-dithiane, and 2-(2,2-bis(mercaptomethylthio)ethyl)-1,3-dithietane.

Examples of the polyamine compound include primary polyamine compounds such as ethylene diamine, 1,2-, or 1,3-diaminopropane, 1,2-, 1,3-, or 1,4-diaminobutane, 1,5-diaminopentane, 1,6-diaminohexane, 1,7-diaminoheptane, 1,8-diaminooctane, 1,10-diaminodecane, 1,2-, 1,3-, or 1,4-diaminocyclohexane, o-, m- or p-diaminobenzene, 3,4- or 4,4'-diaminobenzophenone, 3,4- or 4,4'-diaminodiphenyl ether, 4,4'-diaminodiphenylmethane, 4,4'-diaminodiphenylsulfide, 3,3'- or 4,4'-diaminodiphenylsulfone, 2,7-diaminofluorene, 1,5-, 1,8-, or 2,3-diaminonaphthalene, 2,3-, 2,6-, or 3,4-diaminopyridine, 2,4- or 2,6-diaminotoluene, m-, or p-xylylenediamine, isophoronediamine, diaminomethylbicycloheptane, 1,3- or 1,4-diaminomethylcyclohexane, 2- or 4-aminopiperidine, 2- or 4-aminomethylpiperidine, 2- or 4-aminoethylpiperidine, N-aminoethylmorpholine, and N-aminopropylmorpholine;

monofunctional secondary amine compounds such as diethylamine, dipropylamine, di-n-butylamine, di-sec-butylamine, diisobutylamine, di-n-pentylamine, di-3-pentylamine, dihexylamine, dioctylamine, di(2-ethylhexyl) amine, methylhexylamine, diallylamine, N-methylallylamine, piperidine, pyrrolidine, diphenylamine, N-methylamine, N-ethylamine, dibenzylamine, N-methylbenzylamine, N-ethylbenzylamine, dicyclohexylamine, N-methylaniline, N-ethylaniline, dinaphthylamine, 1-methylpiperazine, and morpholine; and secondary polyamine compounds such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diamino-pentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,5-diaminopentane, N,N'-diethyl-1,6-diaminohexane, N,N'-diethyl-1,7-diaminoheptane, piperazine, 2-methylpiperazine, 2,5-dimethylpiperazine, 2,6-dimethylpiperazine, homopiperazine, 1,1-di-(4-piperidyl)methane, 1,2-di-(4-piperidyl)ethane, 1,3-di-(4-piperidyl)propane, 1,4-di-(4-piperidyl)butane, and tetramethylguanidine.

Examples of the acid anhydride include succinic anhydride, phthalic anhydride, maleic anhydride, tetrabromophthalic anhydride, tetrahydrophthalic anhydride, trimellitic anhydride, and dodecylsuccinic anhydride.

Examples of the polycarboxylic acid compound include succinic acid, adipic acid, sebacic acid, azelaic acid, dodecanedioic acid, terephthalic acid, isophthalic acid, orthophthalic acid, phthalic anhydride, tetrahydrophthalic acid, hexahydrophthalic acid, naphthalene dicarboxylic acid, biphenyl dicarboxylic acid, dimer acid, trimellitic acid, pyromellitic acid, and ε-caprolactone.

The above polymerization reactive compounds may be used alone or two or more thereof may be used in combination.

The polymerization reactive compound included in the composition of the present invention will be described in more detail below. The polymerization reactive compound can be classified into Group A and Group B according to reactivity.

Group A: a polyiso(thio)cyanate compound, a poly(thio) epoxy compound, a polyoxetanyl compound, a polythietanyl compound, a poly(meth)acryloyl compound, a polyalkene compound, or an alkyne compound can be classified into Group A as a self-polymerizable or copolymerizable compound. Here, the following Group B is not included in Group A.

Group B: a poly(thi)ol compound, a polyamine compound, an acid anhydride, or a polycarboxylic acid compound can be classified into Group B as an addition-polymerizable compound. Here, the above Group A is not included in Group B.

In a case where the polymerization reactive compound is used alone, any one selected from Group A or Group B is selected. In a case where the polymerization reactive compound is used alone (one type), one selected from Group A which is a self-polymerizable or copolymerizable is more easily cured than one selected from Group B which is an addition-polymerizable, and thus this is preferable.

In a case where two or more polymerization reactive compounds are used, a method of mixing two or more selected from only Group A, two or more selected from only Group B, or one or more selected from Group A and one or more selected from Group B can be exemplified. In a case where both Group A and Group B are used, the cured resin tends to adhere to the mold formed of glass or metal, and thus, in particular, the internal release agent of the present invention is required in many cases.

The polyiso(thio)cyanate compound classified into a self-polymerizable or copolymerizable compound tends to have lower self-polymerizability than other compounds classified into Group A or lower reactivity of copolymerization with Group A compounds, and if selecting conditions, a self-polymerization reaction type polymer such as a 1-nylon type polymer or an isocyanurate type polymer is obtained in some cases. Also in the copolymerization with a poly(thio) epoxy compound, an ethylene carbonate type copolymerization polymer is obtained in some cases.

Even in the case of selecting two or more types from only the addition-polymerizable Group B, in general, polymerization is difficult, but in a case where an acid anhydride and a poly(thi)ol compound are used in combination, in a case where an acid anhydride and a polyamine compound are used in combination, or in a case where three types of acid anhydride, poly(thi)ol compound, and polyamine compound are used in combination, there is a tendency that polymerization reaction is likely to proceed, and a curable resin is obtained. The blending ratio between acid anhydride and poly(thi)ol or polyamine is within a range of about 8/2 to 2/8, preferably within a range of 6/4 to 4/6, and more preferably within a range of range of 55/45 to 45/55, in the functional group molar ratio of the acid anhydride group of an acid anhydride/the mercapto group of poly(thi)ol (or amino group of polyamine).

The blending ratio in a case where both Group A and Group B are used is within a range of about 999/1 to 1/9, preferably within a range of 99/1 to 10/90, more preferably within a range of 9/1 to 3/7, and most preferably within a range of 7/3 to 4/6, when expressed in the functional group molar ratio of the polymerizable functional group of Group A/the polymerizable functional group of Group B.

[Other Components Such as Additives]

The composition of the present invention may include components other than the polymerization reactive compound described above. Examples thereof include a monofunctional iso(thio)cyanate compound, a monofunctional (thio)epoxy compound, a monofunctional oxetanyl compound, a monofunctional thietanyl compound, a monofunctional (meth)acryloyl compound having one functional group arbitrarily selected from a methacryloyloxy group, an acryloyloxy group, a methacryloylthio group, an acryloylthio group, a methacrylamide group, and an acrylamide group, a monofunctional alkene compound having one polymerizable carbon-carbon double bond other than a methacryloyloxy group, an acryloyloxy group, a methacryloyloxythio group, an acryloylthio group, a methacrylamide group, and an acrylamide group, a monofunctional alcohol compound other than alcohols used as a solvent, a monofunctional thiol compound, a monofunctional amine compound having one functional group arbitrarily selected from an amino group and a secondary amino group, a monofunctional carboxylic acid compound having one carboxyl group, a solvent, and water.

Here, when the molded product of the present invention is produced by cast polymerization, if a large amount of residual solvent and moisture remain in the composition, bubbles are likely to be occur during injection and polymerization curing, and finally, bubbles are fixed (solidified) inside the molded product, and thus, it is preferable that a solvent and water are not included in the composition including the polymerization reactive compound as much as possible. Accordingly, the amount of the solvent and water included in the composition of the present invention immediately before being injected into a cavity is preferably at least 20% by weight or less, more preferably 5% by weight or less, and still more preferably 1% by weight or less.

Examples of the solvent highly capable of being included in the composition of the present invention include solvents mixed in various routes such as a reaction solvent remaining in the phosphodiester compound A for internal release agents represented by the general formula (1) of the present invention, a reaction solvent remaining in the polymerizable compound, a solvent added for the purpose of lowering the viscosity of the composition, and a solvent added for dissolving various additives for the purpose of improving operability.

Examples of the type of solvent which is highly likely to remain include water such as moisture, alcohols such as methanol, ethanol, 1-propanol, isopropanol, 1-butanol, isobutanol, t-butanol, 1-pentanol, 2-pentanol, 3-pentanol, isopentanol, 1-hexanol, 2-ethylhaxanol, 1-octanol, 2-methoxyethanol, and 1-methoxy-2-propanol, ketones such as acetone, methyl ethyl ketone, methyl-n-propyl ketone, methyl isopropyl ketone, methyl-n-butyl ketone, methyl isobutyl ketone, and cyclohexanone, esters such as ethyl acetate, n-propyl acetate, isopropyl acetate, n-butyl acetate, and isobutyl acetate, carbonates such as diethyl carbonate, ethylene carbonate, and 1,2-propylene carbonate, ethers such as diethyl ether, di-n-propyl ether, diisopropyl ether, di-n-butyl ether, tetrahydrofuran, and dioxane, aliphatic hydrocarbons such as n-hexane, cyclohexane, and methylcyclohexane, aromatic hydrocarbons such as benzene, toluene, and xylene, nitrogen-containing compounds such as N, N-dimethylformamide, N, N-dimethylacetamide, n-methylpyrrolidone, and nitrobenzene, and halogen-containing compounds such as dichloromethane, chloroform, dichloroethane, 1,1,2-trichloro-1,1,2-trifluoroethane, and 1,1,2,2-tetrachloro-1,2-difluoroethane In the process for producing a molded product by cast-polymerizing the composition of the present invention, as necessary, in the case of being cured by heat, a polymerization catalyst or a thermal polymerization initiator is added, and in the case of being cured by radiation other than infrared rays (heat), such as ultraviolet rays, a photopolymerization initiator is added.

Examples of the polymerization catalyst include a tertiary amine compound and an inorganic acid salt or an organic acid salt thereof, a metal compound, a quaternary ammonium salt, and an organic sulfonic acid.

The amount of polymerization catalyst used is preferably within a range of 5 ppm to 15% by weight, more preferably within a range of 10 ppm to 10% by weight, and still more preferably within a range of 50 ppm to 3% by weight, with respect to the composition.

Examples of the thermal polymerization initiator used include ketone peroxide compounds such as methyl isobutyl ketone peroxide and cyclohexanone peroxide;

diacyl peroxide compounds such as isobutyryl peroxide, o-chlorobenzoyl peroxide, and benzoyl peroxide;

dialkyl peroxide compounds such as tris(t-butylperoxy) triazine and t-buthyl cumyl peroxide;

peroxyketal compounds such as 1,1-di(t-hexylperoxy) cyclohexane, 2,2-bis(4,4-di-t-butylperoxycyclohexyl) propane, and 2,2-di(t-butylperoxy) butane;

alkyl perester compounds such as α-cumylperoxyneodecanoate, t-butylperoxypivalate, 2,4,4-trimethylphenylperoxy-2-ethyl hexanoate, t-butylperoxy-2-ethyl hexanoate, and t-butylperoxy-3,5,5-trimethyl hexanoate; and peroxycarbonate compounds such as di-3-methoxybutyl peroxydicarbonate, bis(4-t-butylcyclohexyl) peroxydicarbonate, t-butyl peroxyisopropyl carbonate, and diethylene glycol bis(t-butylperoxycarbonate).

Examples of the photopolymerization initiator include a photoradical polymerization initiator, a photocationic polymerization initiator, and a photoanionic polymerization initiator, and among these photopolymerization initiators, a photoradical polymerization initiator is preferable.

Examples of the photoradical polymerization initiator include Irgacure 127 (manufactured by BASF Corp.), Irgacure 651 (manufactured by BASF Corp.), Irgacure 184 (manufactured by BASF Corp.), Darocure 1173 (manufactured by BASF Corp.), benzophenone, 4-phenyl benzophenone, Irgacure 500 (manufactured by BASF Corp.), Irgacure 2959 (manufactured by BASF Corp.), Irgacure 907 (manufactured by BASF Corp.), Irgacure 369 (manufactured by BASF Corp.), Irgacure 1300 (manufactured by BASF Corp.), Irgacure 819 (manufactured by BASF Corp.), Irgacure 1800 (manufactured by BASF Corp.), Darocure TPO (manufactured by BASF Corp.), Darocure 4265 (manufactured by BASF Corp.), Irgacure OXE01 (manufactured by BASF Corp.), Irgacure OXE02 (manufactured by BASF Corp.), Esacure KT55 (manufactured by Lamberti S.p.A.), Esacure ONE (manufactured by Lamberti S.p.A.), Esacure KIP150 (manufactured by Lamberti S.p.A.), Esacure KIP100F (manufactured by Lamberti S.p.A.), Esacure KT37 (manufactured by Lamberti S.p.A.), Esacure KT046 (manufactured by Lamberti S.p.A.), Esacure 1001M (manufactured by Lamberti S.p.A.), Esacure KIP/EM (manufactured by Lamberti S.p.A.), Esacure DP250 (manufactured by Lamberti S.p.A.), Esacure KB1 (manufactured by Lamberti S.p.A.), and 2,4-diethyl thioxanthone.

Among these photoradical polymerization initiators, Irgacure 127 (manufactured by BASF Corp.), Irgacure 184 (manufactured by BASF Corp.), Darocure 1173 (manufactured by BASF Corp.), Irgacure 500 (manufactured by BASF Corp.), Irgacure 819 (manufactured by BASF Corp.), Darocur TPO (manufactured by BASF Corp.), Esacure ONE (manufactured by Lamberti S.p.A.), Esacure KIP100F (manufactured by Lamberti S.p.A.), Esacure KT37 (manufactured by Lamberti S.p.A.), or Esacure KT046 (manufactured by Lamberti S.p.A.) is preferable.

Examples of the photocationic polymerization initiator include Irgacure 250 (manufactured by BASF Corp.), Irgacure 784 (manufactured by BASF Corp.), Esacure 1064 (manufactured by Lamberti S.p.A.), CYRAURE UV16990 (manufactured by Union Carbide Corporation Japan), ADEKA OPTOMER SP-172 (manufactured by ADEKA CORPORATION), ADEKA OPTOMER SP-170 (manufactured by ADEKA CORPORATION), ADEKA OPTOMER SP-152 (manufactured by ADEKA CORPORATION), and ADEKA OPTOMER SP-150 (manufactured by ADEKA CORPORATION).

In a case where the above-described photopolymerization initiator is used, a photopolymerization accelerator may be used in combination. Examples of the photopolymerization accelerator include 2,2-bis(2-chlorophenyl)-4,5'-tetraphenyl-2'H-<1,2'>biimidazolyl, tris(4-dimethylaminophenyl) methane, 4,4'-bis(dimethylamino) benzophenone, 2-ethylanthraquinone, and camphorquinone.

The amount of the photopolymerization initiator and the thermal polymerization initiator used is preferably within a range of 0.1 to 20% by weight, more preferably within a range of 0.5 to 10% by weight, and still more preferably within a range of 1 to 5% by weight, in the composition.

To prevent changing in quality even in a case where a molded product comprised of the curable resin of the present invention is exposed to the outside for a long period of time, it is desirable that by further adding an ultraviolet absorber and a hindered amine-based stabilizer to the composition of the present invention, a composition at which weather resistance is imparted is obtained.

The ultraviolet absorber is not particularly limited, and for example, various ultraviolet absorbers such as a benzotriazole-based ultraviolet absorber, a triazine-based ultraviolet absorber, a benzophenone-based ultraviolet absorber, a benzoate-based ultraviolet absorber, a propanedioic acid ester-based ultraviolet absorber, and an oxanilide-based ultraviolet absorber can be used.

Specific examples thereof include benzotriazole-based ultraviolet absorbers such as 2-(2H-benzotriazol-2-yl)-4-methyl-6-(3,4,5,6-tetrahydrophthalibizylmethyl)phenol, 2-(2H-benzotriazol-2-yl)-p-cresol, 2-(2H-benzotriazol-2-yl)-4-tert-butylphenol, 2-(2H-benzotriazol-2-yl)-4,6-di-tert-butylphenol, 2-(2H-benzotriazol-2-yl)-4,6-bis(1-methyl-1-phenylethyl)phenol, 2-(2H-benzotriazol-2-yl)-4-(1,1,3,3-tetramethylbutyl)-6-(1-methyl-1-phenylethyl)phenol, 2-(2H-benzotriazol-2-yl)-4-(3-one-4-oxa-dodecyl)-6-tert-butyl-phenol, 2-{5-chloro(2H)-benzotriazol-2-yl}-4-(3-one-4-oxa-dodecyl)-6-tert-butyl-phenol, 2-{5-chloro (2H)-benzotriazol-2-yl}-4-methyl-6-tert-butyl-phenol, 2-(2H-benzotriazol-2-yl)-4,6-di-tert-pentyl phenol, 2-{5-chloro (2H)-benzotriazol-2-yl}-4,6-di-tert-butylphenol, 2-(2H-benzotriazol-2-yl)-4-tert-octylphenol, 2-(2H-benzotriazole-2-yl)-4-methyl-6-n-dodecylphenol, methyl-3-{3-(2H-benzotriazol-2-yl)-5-tert-butyl-4-hydroxyphenyl}propionate, a reaction product of polyethylene glycol 300, product name Viosorb 583 (manufactured by KYODO CHEMICAL CO., LTD.), product name Tinuvin 326 (manufactured by BASF Corp.), product name Tinuvin 384-2 (manufactured by BASF Corp.), product name Tinuvin PS (manufactured by BASF Corp.), and product name Seesorb706 (manufactured by SHIPRO KASEI KAISHA LTD.); triazine-based ultraviolet absorbers such as 2-(4-phenoxy-2-hydroxy-phenyl)-4,6-diphenyl-1,3,5-triazine, 2-(2-hydroxy-4-oxa-hexadesiloxy)-4,6-di(2,4-dimethyl-phenyl)-1, 3,5-triazine, 2-(2-hydroxy-4-oxa-heptadesiloxy)-4,6-di(2,4-dimethyl-phenyl)-1, 3,5-triazine, 2-(2-hydroxy-4-iso-octyloxy-phenyl)-4,6-di(2,4-dimethyl-phenyl)-1,3,5-triazine, product name Tinuvin 400 (manufactured by BASF Corp.), product name Tinuvin 405 (manufactured by BASF Corp.), product name Tinuvin 460 (manufactured by BASF Corp.), and product name Tinuvin 479 (manufactured by BASF Corp.); benzophenone-based ultraviolet absorbers such as 2-hydroxy-4-n-methoxybenzophenone and 2-hydroxy-4-n-octoxybenzophenone; benzoate-based ultraviolet absorbers such as 2,4-di-tert-butylphenyl-3,5-di-tert-butyl-4-hydroxybenzoate; propanedioic acid ester-based ultraviolet absorbers such as propanedioic acid-{(4-methoxyphenyl)-methylene}-dimethyl ester, product name Hostavin PR-25 (manufactured by Clariant Japan K.K.), and product Name Hostavin B-CAP (manufactured by Clariant Japan K.K.); and oxanilide-based ultraviolet absorbers such as 2-ethyl-2'-ethoxy-oxanilide and product Name Sanduvor VSU (manufactured by Clariant Japan K.K.). Among these ultraviolet absorbers, benzotriazole-based ultraviolet absorbers or triazine-based ultraviolet absorbers are preferable.

The hindered amine light stabilizers (abbreviated as HALS) are not particularly limited, and, in general, are expressed as a generic term for compounds having a 2,2,6,6-tetramethylpiperidine skeleton in many cases, and depending on the molecular weight, the hindered amine light stabilizers broadly divided into a low molecular weight HALS, a medium molecular weight HALS, a high molecular weight HALS, and a reactive HALS.

Specific examples of the hindered amine light stabilizers include product name TINUVIN 111 FDL (manufactured by BASF Corp.), bis(1-octyloxy-2,2,6,6-tetramethyl-4-piperidyl) sebacate (product name Tinuvin 123 (manufactured by BASF Corp.)), product name TINUVIN 144 (manufactured by BASF Corp.), product name TINUVIN 292 (manufactured by BASF Corp.), product name TINUVIN 765 (manufactured by BASF Corp.), product name TINUVIN 770 (manufactured by BASF Corp.), N,N'-bis(3-aminopropyl) ethylenediamine-2,4-bis[N-butyl-N-(1,2,2,6,6-pentamethyl-4-piperidyl)amino]-6-chloro-1,3,5-triazine condensate (product name CHIMASSORB 119 FL (manufactured by BASF Corp.)), product name CHIMASSORB 2020 FDL (manufactured by BASF Corp.), dimethyl succinate-1-(2-hydroxyethyl)-4-hydroxy-2,2,6,6-tetramethylpiperidine polycondensate (product name CHIMASSORB 622 LD (manufactured by BASF Corp.)), poly[{6-(1,1,3,3-tetramethyl-butyl)amino-1,3,5-triazine-2,4-diyl}{(2,2,6,6-tetramethyl-4-piperidyl)imino}hexamethylene{(2,2,6,6-tetramethyllauryl-4-piperidyl)imino}] (product name CHIMASSORB 944 FD (manufactured by BASF Corp.)), product name Sanduvor 3050 Liq. (manufactured by Clariant Japan K.K.), product name Sanduvor 3052 Liq. (manufactured by Clariant Japan K.K.), product name Sanduvor 3058 Liq. (manufactured by Clariant Japan K.K.), product name Sanduvor 3051 Powder. (manufactured by Clariant Japan K. K.), product name Sanduvor 3070 Powder. (manufactured by Clariant Japan K.K.), product name VP Sanduvor PR-31 (manufactured by Clariant Japan K.K.), product name Hostavin N 20 (manufactured by Clariant Japan K.K.), product name Hostavin N 24 (manufactured by Clariant Japan K.K.), product name Hostavin N 30 (manufactured by Clariant Japan K. K.), product name Hostavin N 321 (manufactured by Clariant Japan K.K.), product name Hostavin PR-31 (manufactured by Clariant Japan K.K.), product name Hostavin 845 (manufactured by Clariant Japan K.K.), and product name Nylostab S-EED (manufactured by Clariant Japan K.K.).

The addition amount of the ultraviolet absorber and the hindered amine light stabilizer is not particularly limited, and the ultraviolet absorber in the composition is usually in a range of 0.1 to 20% by weight, and preferably 0.5 to 10% by weight, and the hindered amine light stabilizer is usually in a range of 0.1 to 10% by weight, preferably 0.5 to 5% by weight, and more preferably 1 to 3% by weight. In a case where the addition amount of the ultraviolet absorber and the hindered amine light stabilizer is within the above-described range, the effect of improving the weather resistance of the cured resin obtained by polymerizing the composition of the present invention and the molded product comprised of the resin becomes large. In a case where the addition amount of the ultraviolet absorber and the hindered amine light stabilizer is less than the above-described range, the effect of improving the weather resistance of the molded product obtained tends to be decrease. On the other hand, in a case where the addition amount of the ultraviolet absorber and the hindered amine light stabilizer is greater than the above-described range, it may be insufficient when the composition including the polymerization reactive compound is polymerized with radiation with such as W.

Furthermore, for the purpose of imparting dimming properties, a light control dye or a light control pigment may be added. As a representative light control dye or light control pigment, for example, at least one kind of compound selected from a spiropyran-based compound, a spirooxazine-based compound, a fulgide-based compound, a naphthopyran-based compound, and a bisimidazole compound can be used depending on the desired color.

Examples of the spiropyran-based compound include each substitute obtained by substituting the indole ring or the benzene ring of indolinospirobenzopyran with a halogen atom, a methyl group, an ethyl group, a methylene group, an ethylene group, or a hydroxyl group, each substitute obtained by substituting the indole ring or the naphthalene ring of indolinospironaphthopyran with a halogen atom, a methyl group, an ethyl group, a methylene group, an ethylene group, or a hydroxyl group, each substitute obtained by substituting the indole ring of indolinospiroquinolinopyran with a halogen atom, a methyl group, an ethyl group, a methylene group, an ethylene group, or a hydroxyl group, and each substitute obtained by substituting the indole ring of indolinospiropyridopyran with a halogen atom, a methyl group, an ethyl group, a methylene group, an ethylene group, or a hydroxyl group.

Examples of the spirooxazine-based compound include each substitute obtained by substituting the indole ring or the benzene ring of indolinospirobenzoxazine with a halogen atom, a methyl group, an ethyl group, a methylene group, an ethylene group, or a hydroxyl group, each substitute obtained by substituting the indole ring or the naphthalene ring of indolinospironaphthoxazine with a halogen atom, a methyl group, an ethyl group, a methylene group, an ethylene group, or a hydroxyl group, each substitute obtained by substituting the indole ring of indolinospirophenanthroxazine with a halogen atom, a methyl group, an ethyl group, a methylene group, an ethylene group, or a hydroxyl group, each substitute obtained by substituting the indole ring of indolinospiroquinolinoxazine with a halogen atom, a methyl group, an ethyl group, a methylene group, an ethylene group, or a hydroxyl group, and each substitute obtained by substituting the piperidine ring and the naphthalene ring of piperidinospironaphthoxazine with a halogen atom, a methyl group, an ethyl group, a methylene group, an ethylene group, or a hydroxyl group.

Examples of the fulgide-based compound include N-cyanomethyl-6,7-dihydro-4-methyl-2-phenylspiro(5,6-benzo [b]thiophenedicarboximide-7,2'-tricyclo[3.3.1.1$^{3,7}$]decane], N-cyanomethyl-6,7-dihydro-2-(p-methoxyphenyl)-4-methylspiro(5,6-benzo[b]thiophene-dicarboximide-7,2'-tricyclo [3.3.1.1$^{3,7}$]decane), 6,7-dihydro-N-methoxycarbonylmethyl-4-methyl-2-phenylspiro(5,6-benzo[b]thiophene-dicarboximide-7,2'-tricyclo[3.3.1.1$^{3,7}$]decane), 6,7-dihydro-4-methyl-2-(p-methylphenyl)-N-nitromethylspiro(5,6-benzo[b]thiophenedicarboximide-7,2'-tricyclo[3.3.1.1$^{3,7}$] decane), N-cyanomethyl-6,7-dihydro-4-cyclopropyl-3-methylspiro(5,6-benzo[b]thiophenedicarboximide-7,2'-tricyclo[3.3.1.1$^{3,7}$]decane), N-cyanomethyl-6,7-dihydro-4-cyclopropylspiro(5,6-benzo[b]thiophenedicarboximide-7,2'-tricyclo[3.3.1.1$^{3,7}$]decane), and N-cyanomethyl-6,7-dihydro-2-(p-methoxyphenyl)-4-cyclopropylspiro (5,6-benzo[b]thiophenedicarboximide-7,2'-tricyclo[3.3.1.1$^{3,7}$] decane).

Examples of the naphthopyran-based compound include spiro[norbornane-2,2'-[2H]benzo[h]chromene], spiro[bicyclo[3.3.1]nonane-9,2'-[2H]benzo[h]chromene], 7'-methoxyspiro[bicyclo[3.3.1]nonane-9,2'-[2H]benzo[h]chromene], 7'-methoxyspiro[norbornane-2,2'-[2H]benzo[f]chromene], 2,2-dimethyl-7-octoxy[2H]benzo[h]chromene, spiro[2-bicyclo[3.3.1]nonene-9,2'-[2H]benzo[h]chromene], spiro[2-bicyclo[3.3.1]nonene-9,2'-[2H]benzo[f]chromene], 6-morpholino-3,3-bis(3-fluoro-4-methoxyphenyl)-3H-benzo (f) chromene, and 5-isopropyl-2,2-diphenyl-2H-benzo (h) chromene.

The addition amount of these light control dyes or light control pigments is not particularly limited, and the amount is in a range of about 0.01 to 10000 ppm (by weight), preferably in a range of 0.1 to 1000 ppm (by weight), and more preferably in a range of 1 to 100 ppm (by weight), with respect to the composition including the polymerization reactive compound.

As necessary, various additives such as a polymerization accelerator, a catalyst, an infrared absorbent, a radical scavenger, an antioxidant, a polymerization inhibitor, a pigment and a dye that are not dimming, a binder, a dispersant, a leveling agent, and organic or inorganic particles having a nanometer size may be further added to the composition of the present invention.

The curable resin of the present invention and the molded product comprised of the resin are produced by adding a polymerization reactive compound and as necessary, various additives described above. In addition, a polymerization reactive compound and an additive which are not described in the present application may be added to the composition of the present invention may be added within a range not impairing the effects of the present invention.

As the curable resin configuring the molded product of the present invention, curable resins obtained from a liquid composition of which casting work is easy are preferable, and among these curable resins, curable resins described as the following (a) to (z) are preferable.

(a) a poly(thio)urethane resin obtained by polymerization of a polyiso(thio)cyanate compound and a poly(thi)ol compound In the present application, a poly(thio)urethane resin means a polyurethane resin, a polythiourethane resin, or a polydithiourethane resin.

(b) a poly(thio)urethane resin obtained by polymerization of a polyisocyanate compound or a polyisothiocyanate compound and a polyamine compound In the present application, a poly(thio)urea resin means a polyurea resin or a polythiourea resin.

(c) a poly(thio)epoxy resin obtained by polymerization of a poly(thio)epoxy compound (d) a poly(thio)epoxy-poly(thi)ol resin obtained by polymerization of a poly(thio)epoxy compound and a poly (thi)ol compound (e) a poly(thio)epoxy-polyamine resin obtained by polymerization of a poly(thio)epoxy compound and a polyamine compound (f) a poly(thio)epoxy-acid anhydride resin obtained by polymerization of a poly(thio)epoxy compound and an acid anhydride (g) a poly(meth)acryloyl resin obtained by polymerization of a poly(meth)acryloyl compound (h) a poly(meth)acryloyl-poly(thi)ol resin obtained by polymerization of a poly(meth)acryloyl compound and a poly(thi)ol compound (i) a poly(meth)acryloyl-polyalkene resin obtained by polymerization of a poly(meth)acryloyl compound and a polyalkene compound (j) a poly(meth)acryloyl-polyalkyne resin obtained by polymerization of a poly(meth)acryloyl compound and an alkyne compound (k) a poly(meth)acryloyl-polyamine resin obtained by polymerization of a poly(meth)acryloyl compound and a polyamine compound (l) a polyalkene resin obtained by polymerization of a polyalkene compound (m) a polyalkene-poly(thi)ol resin obtained by polymerization of a polyalkene compound and a poly(thi)ol compound (n) a polyalkene-polyamine resin obtained by polymerization of a polyalkene compound and a polyamine compound (o) a polyalkyne resin obtained by polymerization of an alkyne compound (p) a polyalkyne-poly(thi)ol resin obtained by polymerization of an alkyne compound and a poly(thi)ol compound (q) a polyalkyne-polyamine resin obtained by polymerization of an alkyne compound and a polyamine compound (r) a polyalkyne-polyalkene resin obtained by polymerization of an alkyne compound and a polyalkene compound (s) a polyoxetanyl resin obtained by polymerization of a polyoxetanyl compound (t) a polyoxetanyl-poly(thi)ol resin obtained by polymerization of a polyoxetanyl compound and a poly(thi)ol compound (u) a polyoxetanyl-polyamine resin obtained by polymerization of a polyoxetanyl compound and a polyamine compound (v) a polyoxetanyl-acid anhydride resin obtained by polymerization of a polyoxetanyl compound and an acid anhydride (w) a polythietanyl-poly(thi)ol resin obtained by polymerization of a polythietanyl compound and a poly(thi)ol compound (x) a polythietanyl-polyamine resin obtained by polymerization of a polythietanyl compound and a polyamine compound (y) a polythietanyl-acid anhydride resin obtained by polymerization of a polythietanyl compound and an acid anhydride (z) mixed resins obtained by copolymerization of two or more selected from (a) to (y)

Among the curable resins of the above (a) to (z), as more preferable curable resins, the resins described in (a) to (i) and (s) to (z) and mixed resins thereof (a mixture of a copolymer and a resin) are exemplified, and as still more preferable curable resins, the curable resins described in (a) to (f), and (s) to (v), and (z) and mixed resins thereof are exemplified.

<Optical Materials>

In the present invention, molded bodies having a variety of shapes can be obtained by changing molds at the time of polymerization. The molded product of the present invention can be molded in a desired shape, and can be used as various optical materials by providing a coating layer formed as necessary, other members, or the like.

Examples of the optical materials include a plastic lens, a light emitting diode (LED), a prism, an optical fiber, an information recording substrate, a filter, and a light emitting diode.

A plastic lens is particularly suitable.

The plastic lens comprised of the molded product of the present invention will be described below. The plastic lens can be produced in the following manner.

<Production Method of Plastic Lens>

The plastic lens of the present invention is typically produced by a cast polymerization method using the composition described above.

Specifically, first, an internal release agent including at least one phosphodiester compound A represented by the general formula (1) is added to a composition containing a polymerization reactive compound, then, the obtained composition is mixed by stirring, and degassing step is performed under reduced pressure as necessary.

By injecting the obtained composition of the present invention into a cavity in the mold composed of a glass mold and a gasket or a tape and by heating or irradiating with radiation such as ultraviolet rays or the like other than infrared rays to polymerize and cure the composition, a curable resin of the present invention and a plastic lens comprised of the resin are produced.

In a case where a curable resin of the present invention and a plastic lens comprised of the resin are produced by heating, for the purpose of preventing polymerization ununiformity (striae) by convection, polymerization is conducted by slowly heating from a low temperature over a period of several days. As a representative heating condition, for example, a condition in which the temperature is slowly raised from low temperature in a range of 0° C. to 200° C. for 64 hours, similarly, in a range of 5° C. to 150° C. for 40 hours, and similarly, in a range of 20° C. to 120° C. for 16 hours is exemplified.

Similarly, even in a case where polymerization is performed by radiation such as UV, to prevent polymerization ununiformity (striae) by convection, typically, polymerization is slowly conducted by dividing irradiation of radiation or reducing illuminance. For the purpose of making convection not further occur, a dual cure system, which is comprised of a step of cooling after a uniform polymerizable reactive composition is injected into a cavity to form a state in which convection is less likely to occur, a step of irradiating with a weak radiation to form the semi-cured composition which has become a uniform gel state, and a step of heating it to completely cure, is taken in some cases.

For the purpose of completing polymerization or removing the distortion due to residual stress, the plastic lens obtained by releasing from the mold may be subjected to a re-heat treatment (annealing) as required. Typically, the heat treatment is performed within a range of 1 to 24 hours at Tg of the obtained plastic lens to Tg×2 times the temperature. A heat treatment condition of 1 to 16 hours at Tg to Tg×1.5 times the temperature is more preferable, and a heat treatment condition of 1 to 4 hours at Tg to Tg×1.2 times the temperature is still more preferable.

In a case where a curable resin of the present invention and a plastic lens comprised of the resin are produced by radiation, as the radiation, energy rays having a wavelength range within a range of 0.0001 to 800 nm are typically used. The radiation is classified into α rays, β rays, γ rays, X-rays, electron beams, ultraviolet rays, visible light, and the like, and can be suitably selected according to the composition of the mixture and used. Among the radiation, ultraviolet rays is preferable, and the output peak of ultraviolet rays is preferably within a range of 200 to 450 nm, more preferably within a range of 230 to 445 nm, still more preferably within a range of 240 to 430 run, and particularly preferably within a range of 250 to 400 nm. In the case of using ultraviolet rays within the range of the output peak, defects such as yellowing and thermal deformation at the time of polymerization are small, and it is possible to complete the polymerization in a relatively short period of time even in a case where an ultraviolet absorber is added.

In addition, in a case where an ultraviolet absorber and a hindered amine-based stabilizer are added in the composition, there is a tendency that ultraviolet rays having an energy output peak within a range of 250 to 280 nm or within a range 370 to 430 nm is preferably used.

The curable resin of the present invention and the plastic lens comprised of the resin obtained in the above manner may be subjected to processing of imparting various functionalities by providing a functional coat layer such as a hard coat, an anti-reflection coat, a dimming coat, a slipperiness-imparting coat or a slipperiness-imparting treatment, or an antistatic coat to the surface, by performing a dyeing treatment for imparting fashionability, by performing a griding treatment of the surface, the edge, or the like, and by inserting a polarizing film in the interior for the purpose of imparting polarizability or attaching a polarizing film to the surface.

For the purpose of improving adhesion between the functional coat layer and the substrate, the surface of the obtained curable resin of the present invention or the plastic lens comprised of the resin can also be subjected to a corona treatment, an ozone treatment, a low-temperature plasma treatment using oxygen gas or nitrogen gas, a glow discharge treatment, an oxidation treatment by chemicals, or a physical or chemical treatment such as a flame treatment.

Instead of these treatments or in addition to these treatments, a primer layer formed by a primer treatment, an undercoat treatment, or an anchor coat treatment may be provided between the surface of the curable resin of the present invention or the plastic lens comprised of the resin and the outermost layer (air contact surface) formed by the physical or chemical treatment.

As the coating agent used in the primer layer, for example, a coating agent which has a resin such as a polyester-based resin, a polyamide-based resin, a polyurethane-based resin, an epoxy-based resin, a phenol-based resin, a (meth)acrylic resin, a polyvinyl acetate resin, a polyolefin-based resin of polyethlene or polypropylene or a copolymer thereof or a modified resin, or a cellulose-based resin as the main component of vehicle may be used. The coating agent may be any one of a solvent type coating agent and an aqueous type coating agent.

Among these coating agents, a modified polyolefin-based coating agent, an ethyl vinyl alcohol-based coating agent, a polyethylene imine-based coating agent, a polybutadiene-based coating agent, or a polyurethane-based coating agent;

a polyester-based polyurethane emulsion coating agent, a polyvinyl chloride emulsion coating agent, a urethane acryl emulsion coating agent, a silicon acryl emulsion coating agent, a vinyl acetate acryl emulsion coating agent, or an acryl emulsion coating agent; or a styrene-butadiene copolymer latex coating agent, an acrylnitrile-butadiene copolymer latex coating agent, a methyl methacrylate-butadiene copolymer latex coating agent, a chloroprene latex coating agent, a rubber-based latex coating agent of polybutadiene latex, a polyacrylic acid ester latex coating agent, a polyvinylidene chloride latex coating agent, a polybutadiene latex coating agent, or a coating agent comprised of carboxylic acid-modified product latex or dispersion of a resin included in these latex coating agents is preferable.

These coating agents can be applied, for example, by a dip coating method, a spin coating method, or a spray coating method, and the coating amount to a substrate is typically 0.05 $g/m^2$ to 10 $g/m^2$ in the dry state.

Among these coating agents, a polyurethane-based coating agent is more preferable. The polyurethane-based coating agent contains the resin having a urethane bond in the main chain or the side chain. The polyurethane-based coating agent is, for example, a coating agent including polyurethane obtained by reacting polyol such as polyester polyol, polyether polyol, or acrylic polyol with an isocyanate compound.

Among these polyurethane-based coating agents, a polyurethane-based coating agent obtained by mixing polyester polyol such as condensed polyester polyol or lactone-based polyester polyol and an isocyanate compound such as tolylene diisocyanate, hexamethylene diisocyanate, or xylylene diisocyanate is preferable from the viewpoint of excellent adhesion.

The method of mixing a polyol compound and an isocyanate compound is not particularly limited. In addition, the blending ratio is also not particularly limited, but if the isocyanate compound is too small, curing defects occur in some cases, and thus, the OH groups of the polyol compound and the NCO groups of the isocyanate compound are preferably within a range of 2/1 to 1/40 in terms of equivalent.

The curable resin of the present invention may be applied to those other than plastic lenses, and as applications other than plastic lenses, a sheet, a film, and the like produced in the same manner as in plastic lenses using a flat mold are exemplified. The surface of the sheet, the film, or the like comprised of the curable resin of the present invention may be physically or chemically treated in the same manner as in plastic lenses, or the primer layer described above and the functional outermost layer (air contact surface) formed by a physical or chemical treatment may be laminated.

The plastic lens comprised of the curable resin of the present invention may be a laminate including the primer layer between the functional outermost layer (air contact surface) formed by a physical or chemical treatment and the curable resin surface.

The plastic lens of the present invention obtained in the above manner can be used in various lens applications such as an eyeglass lens, a camera lens, a pickup lens, a Fresnel lens, a prism lens, and a lenticular lens. Examples of a particularly preferable application among these include an eyeglass lens, a camera lens, and a pickup lens, having a smooth surface. In furunell lenses and prism lenses with complicated shapes whose surfaces are not smooth, bubbles are likely to be formed near the interface with the mold (after release, near the lens surface), and multilayered lenticular lenses or the like are unlikely to be uniform near the multilayer interface, and thus, in addition to the internal release agent of the present invention, further improvement is required.

The sheet and the film of the present invention obtained in the same manner can be used in various planar member applications requiring high transparency, such as display members including a flat panel and a smart phone panel, film members including a scatterproof film, a specific wavelength-cutting film, and a decorative film, and alternative members to glass such as building window glass, vehicle window glass, and a mirror.

EXAMPLES

Hereinafter, the present invention will be specifically described based on examples, but the present invention is not limited thereto. Evaluation of the molded product and the plastic lens comprised of a curable resin was performed by the following method.

<Refractive Index (ne) and Abbe Number (ve)>

Measurement was performed at 20° C. using a digital precision refractometer KPR-30V manufactured by Shimadzu Corporation.

<Heat Resistance (Tg)>

The glass transition temperature (Tg) was measured by a TMA penetration method (a load of 50 g, 0.5 mmϕ at the tip of a pin, a temperature raising rate of 10° C./min) using a thermomechanical analyzer TMA-60/60H.

<Releasability>

The releasability at the time of peeling off the mold from the molded product at room temperature was evaluated according to the following criteria.

A: Very good

At the time when cooled to room temperature, the entire surface of the adhesion surface between the mold and the molded product has already been naturally peeled off.

B: Good

At the time when cooled to room temperature, a part of surface of the adhesion surface between the mold and the molded product has already been naturally peeled off, and thus, is easily peeled off by releasing operation (by inserting a wedge type release jig to the adhesion surface between the obtained molded product and the mold, the molded product is peeled off from the mold).

C: Slightly Poor

Even in the case of being cooled to room temperature, the mold and the molded product are adhered, and thus, manage to be peeled off by releasing operation (by inserting a wedge type release jig into the contact surface between the obtained molded product and the mold, the molded product is peeled off from the mold). A lens or a mold is defected in some cases.

D: Bad

After being cooled to room temperature, even in a case where releasing operation (by inserting a wedge type release jig into the adhesion surface between the obtained molded product and the mold, the molded product is peeled off from the mold) is performed, the mold and the molded product are adhered.

<Transparency>

A sample (curable resin and plastic lens) was irradiated with light of a halogen lamp output 300 W of CS-15 MT manufactured by Cabin-kogyo Co., Ltd., and evaluation was performed visually.

B: Good (there was no turbidity)

C: Slightly poor (slight turbid)

D: Bad (there was obviously turbid)

Production Example 1

Phosphoric ester (110A) including the following phosphodiester (110) was obtained by the following known method.

Figure 2:
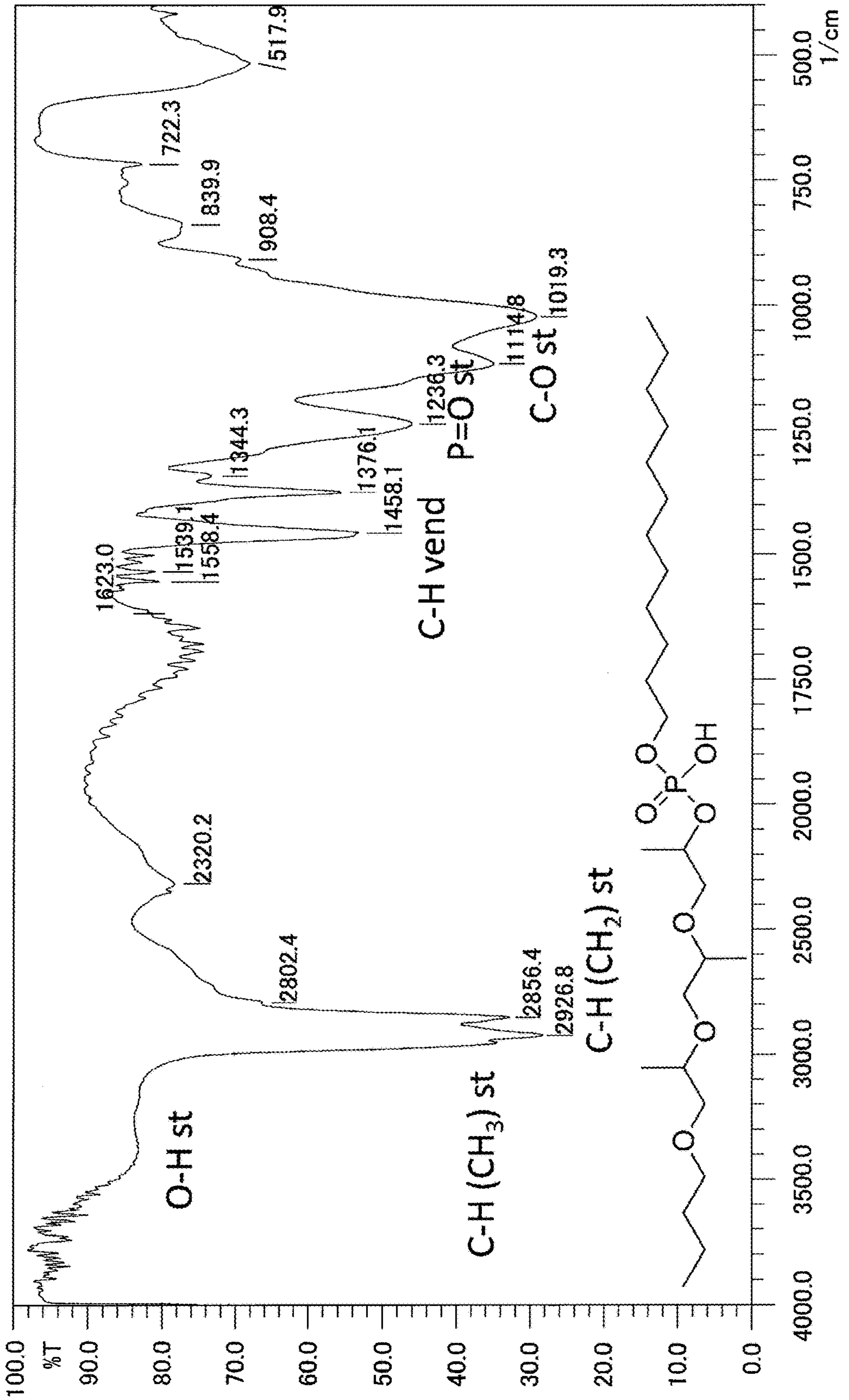
FIG. 2 is an IR spectrum chart of phosphoric ester (110A) including the phosphodiester (110) obtained in Production Example 1.

27.0 g of phosphorus oxychloride (manufactured by Wako Pure Chemical Industries, Ltd.) was dissolved in 30 g of tetrahydrofuran, and the solution was cooled to 0° C. To this solution, a mixed solution of 43.7 g of tri(propyleneglycol) n-butyl ether isomer mixture (DOWANOL TPnB manufactured by The Dow Chemical Company), 17.8 g of triethylamine, and 20 g of tetrahydrofuran was added dropwise over 30 minutes. At the time of dropping, the temperature of the reaction solution was 5° C. to 10° C. After the dropping ended, the solution was aged at 35° C. for 2 hours. Thereafter, the reaction solution was further cooled to 0° C., and a solution of 32.8 g of 1-dodecanol (manufactured by Wako Pure Chemical Industries, Ltd.), 17.8 g of triethylamine, and 20 g of tetrahydrofuran was added dropwise thereto over a period of 30 minutes. At the time of dropping, the temperature of the reaction solution was 5° C. to 10° C. After the dropping, the temperature was slowly raised, and the solution was further aged at 20° C. for 10 hours. After the reaction ended, the reaction solution was cooled to 0° C., a solution obtained by dissolving 28.2 g of sodium hydroxide in 40 g of ion exchange water was added dropwise thereto over a period of 30 minutes, and the solution was stirred at 0° C. for 2 hours. 300 mL of 3N hydrochloric acid was added to the reaction solution to acidify the reaction solution, and then, the produced phosphoric ester was extracted with 200 g of diethyl ether. The organic layer was collected by separation, and then, washed with ion exchange water (100 mL×4). After the organic layer was collected by separation, the solvent was distilled off under reduced pressure, whereby 85.5 g of phosphoric ester (110A) was obtained (1-dodecanol phosphoric acid monoester: phosphodiester (110) represented by the following formula (110)=16:84). Identification data of the phosphodiester (110) is shown in FIG. 1 ($^1$H-NMR spectrum chart) and FIG. 2 (IR spectrum chart).

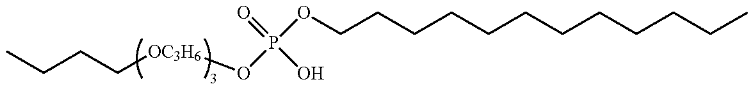

(110)

Production Example 2

The following phosphodiester (100) was obtained by the following known method.

Figure 3:
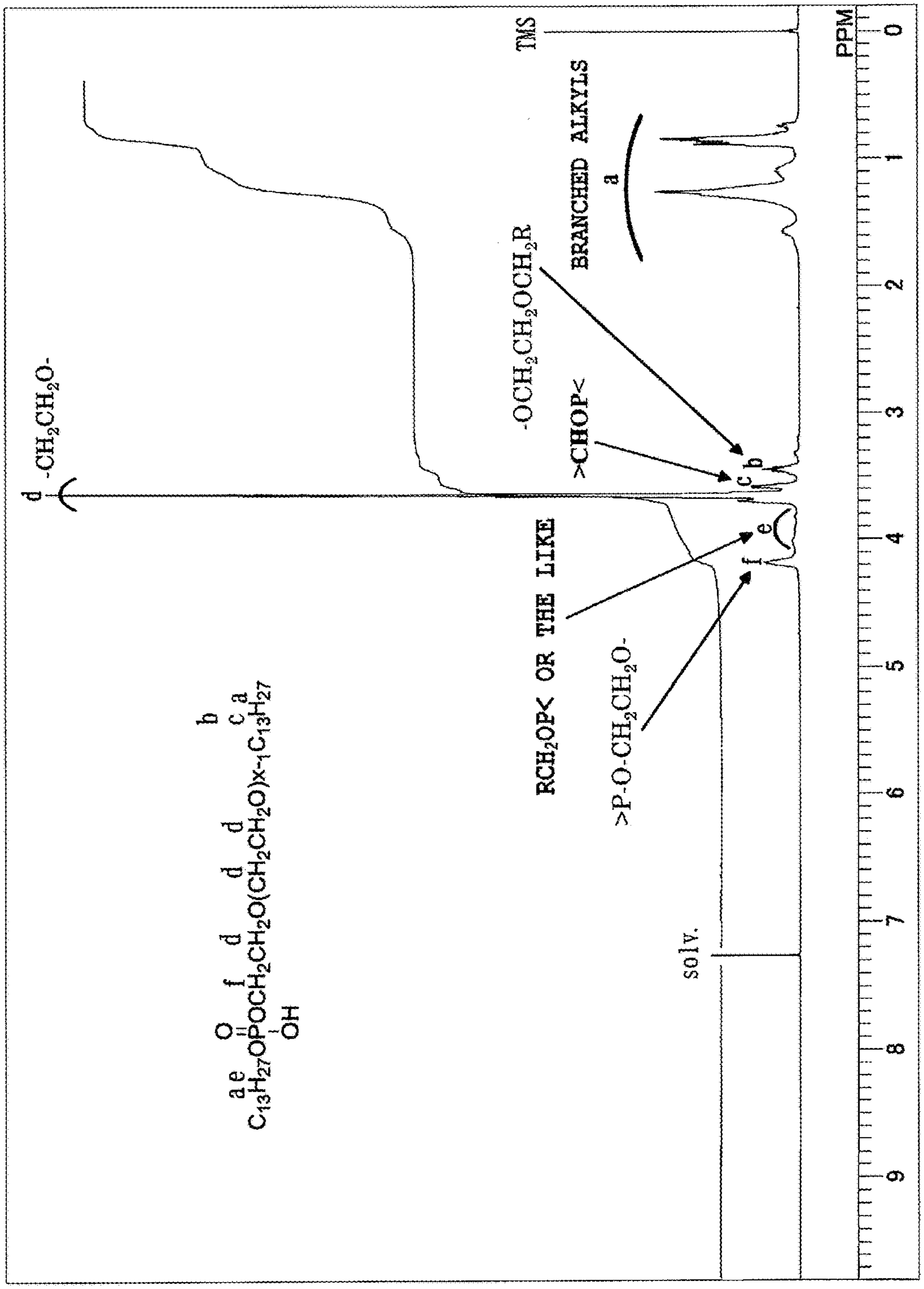
FIG. 3 is a $^{1}$H-NMR spectrum chart of phosphodiester (100) obtained in Production Example 2.
Figure 4:
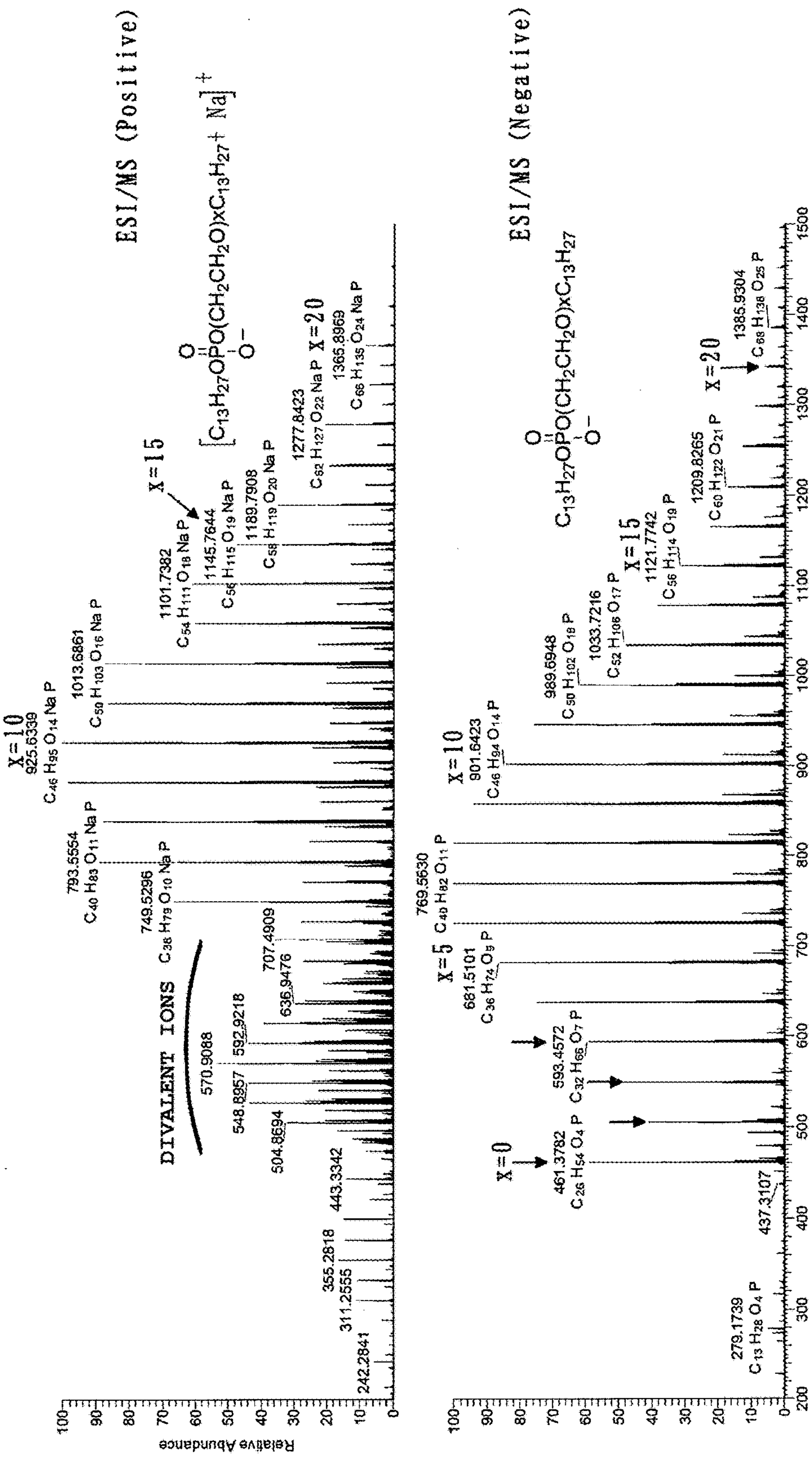
FIG. 4 is an electrospray mass spectrometry chart of the phosphodiester (100) obtained in Production Example 2.
Figure 5:
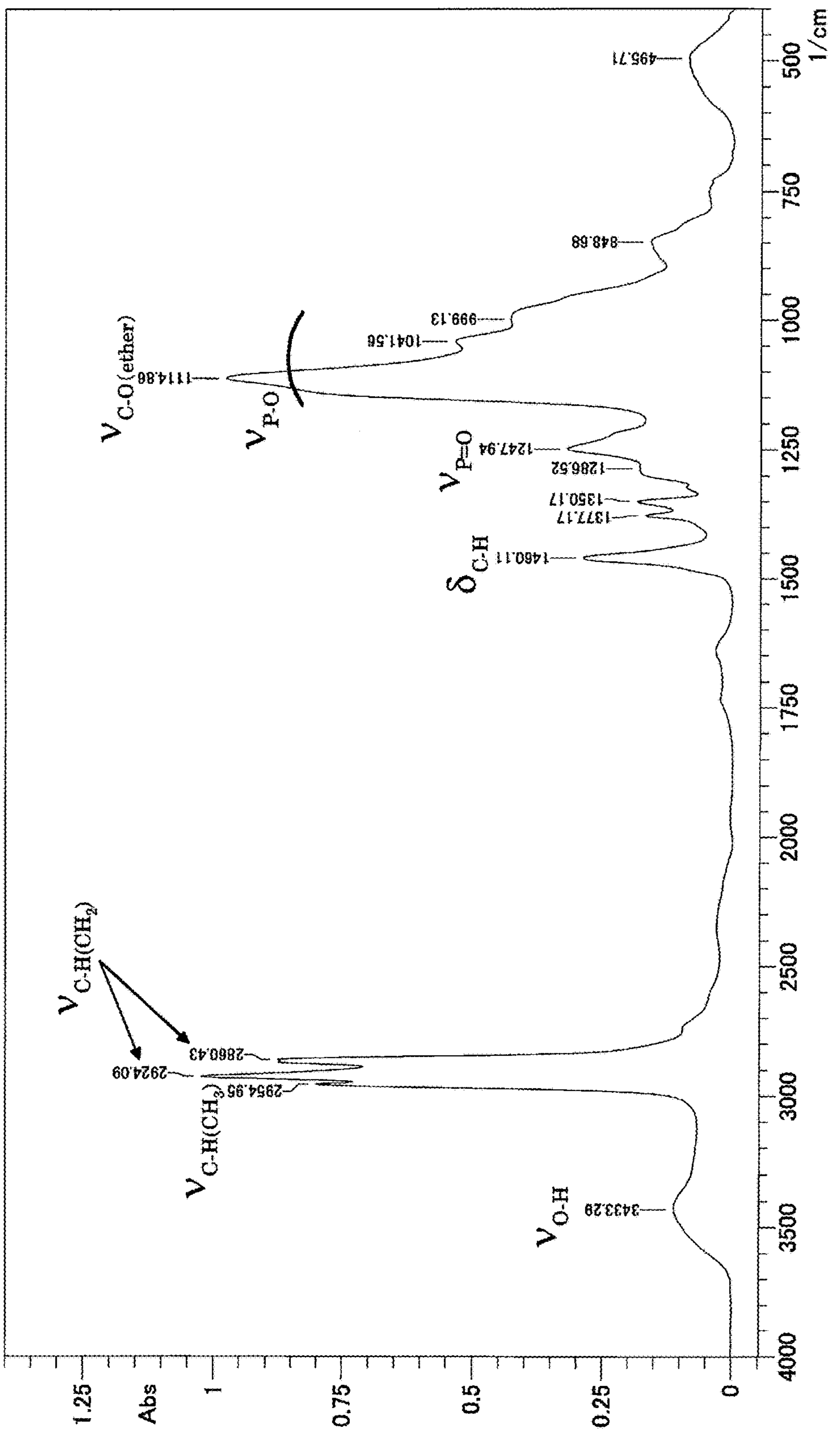
FIG. 5 is an IR spectrum chart of the phosphodiester (100) obtained in Production Example 2.

Synthesis was performed in the same manner as in Production Example 1 except that alcohol (300) and tridecanol respectively represented by the following formula (300) were used instead of the tri(propyleneglycol) n-butyl ether isomer mixture and the 1-dodecanol which were the raw materials, whereby a phosphodiester (100) represented by the following formula (100) was obtained. Identification data of the obtained phosphodiester (100) is shown in FIG. 3 ($^1$H-NMR spectrum chart), FIG. 4 (electrospray mass spectrometry chart), and FIG. 5 (IR spectrum chart).

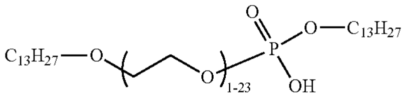

(100)

Production Example 3

According to Japanese Unexamined Patent Publication No.

H04-134088, a phosphodiester (120) represented by the following formula (120) was produced. That is, 100 g of monotrioxyethylenelauryl phosphate, 66.6 g of potassium hydroxide, and 157.0 g of ion exchange water were mixed, and the temperature was raised to 70° C. and dissolve these compounds. To this solution, 117.0 g of diethyl sulfate was added dropwise over a period of 8 hours. After the dropping ended, the solution was aged at 70° C. for 4 hours. The reaction mixture was made to be acidic with hydrochloric acid, and then extracted three times with 250 mL of ether. The residue obtained by distilling ether off under reduced pressure was recrystallized from ethanol, whereby a phosphodiester (120) was obtained.

(120)

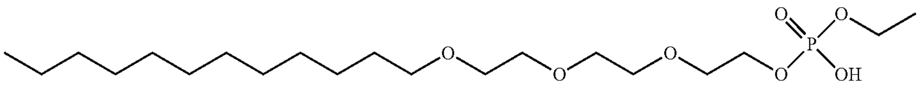

Production Example 4

According to U.S. Pat. No. 3,666,843 A, a phosphodiester (130) represented by the following formula (130) was produced. That is, 300 g of isooctylphenyl nonaoxyethylene glycol and 54 g of ethyl metaphosphate were injected into a reaction vessel, and these were stirred at 70° C. for 3.5 hours, whereby a phosphodiester (130) was obtained.

(130)

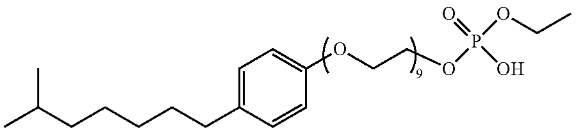

Example 1

0.01 parts by weight (500 ppm) of the phosphodiester (100) represented by the above formula (100) as an internal release agent, 0.3 parts by weight (15,000 ppm) of 2-(2'-hydroxy-5'-t-octylphenyl)benzotriazole (BIOSORB 583, manufactured by KYODO CHEMICAL CO., LTD.) as a UV absorber, 0.01 parts by weight (500 ppm) of dimethyl tin(II) dichloride as a catalyst, and 6.14 parts by weight of tolylene diisocyanate and 3.19 parts by weight of hexamethylene diisocyanate as polymerization reactive compounds were mixed by stirring at 20° C., whereby a homogeneous solution was obtained. To the homogeneous solution, 10.67 parts by weight of a mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane, as a polymerization reactive compound was added and these were mixed by stirring at 20° C., whereby a polymerizable composition was obtained. After degassing the polymerizable composition under reduced pressure of 0.13 kPa for 30 minutes, filtration was performed using a 1 μm PTFE filter, and the polymerizable composition was poured into a cavity (curve shape: 4 curves for both concave and convex surfaces, center thickness: 2 mm) in the mold composed of a glass mold and tape, and sealed with tape. This was put into a polymerization oven, then, slowly heated from 25° C. to 130° C. over a period of 19 hours, and held at 130° C. for 2 hours so as to polymerize this. After cooling, the glass mold and the tape were peeled off, and a molded product (plastic lens) comprised of a curable resin formed inside was taken out. Peeling was very easy, and due to this, there was no deformation such as breakage of the molded product (plastic lens) and damage of the glass mold. The molded product (plastic lens) was colorless and transparent, and had a refractive index ne of 1.67, an Abbe number νe of 28, and Tg of 116° C. Releasability and transparency were confirmed. The results are shown in Table 1.

Example 2

A molded product (plastic lens) was produced in the same manner as in Example 1 except that the amount of the phosphodiester (100) represented by the above formula (100) was changed as described in Table 1, and releasability and transparency were confirmed. The results are shown in Table 1.

TABLE 1

| | | Addition mount (ppm) of phosphodiester (100) | | | | | | | |
|---|---|---|---|---|---|---|---|---|---|
| | | 0 | 20 | 30 | 50 | 100 | 500 | 1,000 | 2,000 |
| Example 1 | Releasability | — | — | — | — | — | A | — | — |
| | Transparency | — | — | — | — | — | B | — | — |
| Example 2 | Releasability | D | B | B | B | B | — | A | A |
| | Transparency | — | B | B | B | B | — | B | B |

Example 3

A molded product (plastic lens) was produced in the same manner as in Example 1 except that phosphoric ester (110A) including the phosphodiester (110) represented by the above formula (110) was used instead of the phosphodiester (100) and the addition amount was changed to 1000 ppm, and releasability and transparency were confirmed. The results are shown in Table 2.

Example 4

A molded product (plastic lens) was produced in the same manner as in Example 1 except that the phosphodiester (120) represented by the above formula (120) was used instead of the phosphodiester (100) and the addition amount was changed to 1000 ppm, and releasability and transparency were confirmed. The results are shown in Table 2.

Example 5

A molded product (plastic lens) was produced in the same manner as in Example 1 except that the phosphodiester (130) represented by the above formula (130) was used instead of the phosphodiester (100) and the addition amount was changed to 1000 ppm, and releasability and transparency were confirmed. The results are shown in Table 2.

TABLE 2

| | | | Addition amount (ppm)* of phosphodiester 1000 |
|---|---|---|---|
| Example 3 | Compound (110) | Releasability | B |
| | | Transparency | B |
| Example 4 | Compound (120) | Releasability | B |
| | | Transparency | B |
| Example 5 | Compound (130) | Releasability | B |
| | | Transparency | B |

*Example 3 is an addition amount of phosphoric ester (110A) including phosphodiester (100)

Production Example 5

An internal release agent A was obtained by the following known method.

First, synthesis was performed in the same manner as in Production Example 1 except that the step of adding the tri(propyleneglycol)n-butyl ether isomer mixture which was the raw material was omitted, and in the step of adding 1-dodecanol, alcohol (300) represented by the following formula (300) was added instead of 1-dodecanol, whereby a phosphoric monoester (200) represented by the following formula (200) was obtained.

16 parts by weight of the phosphodiester (100) obtained in Production Example 2, 16 parts by weight of the phosphoric monoester (200), and 68 parts by weight of the alcohol (300) represented by the following formula (300) were mixed, whereby an internal release agent A.

Internal release agent A (100)

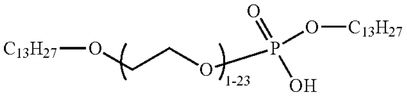

16 wt %

(200)

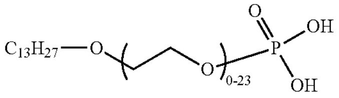

16 wt %

(300)

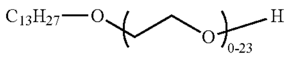

68 wt %

Example 6

A molded product (plastic lens) was produced in the same manner as in Example 1 except that the internal release agent A was used instead of the phosphodiester (100) and the addition amount of the internal release agent A was changed as shown in Table 3, and releasability and transparency were confirmed. The results are shown in Table 3.

Comparative Examples 1 to 3

A molded product (plastic lens) was produced in the same manner as in Example 6 except that the internal release agent B, C, or D including a compound in the following composition ratio was used instead of the internal release agent A, and releasability and transparency were confirmed. The results are shown in Table 3.

The internal release agent B was synthesized based on the description of Japanese Unexamined Patent Publication No. 2000-281687, the internal release agent C was JP-506H manufactured by JOHOKU CHEMICAL CO., LTD., and the internal release agent D was ZelecUN manufactured by STEPAN Company.

Internal release agent B

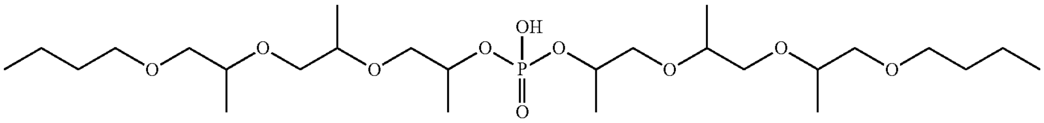

99 wt %

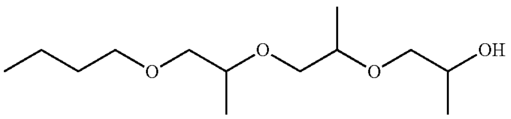

1 wt %

-continued

Internal release agent C

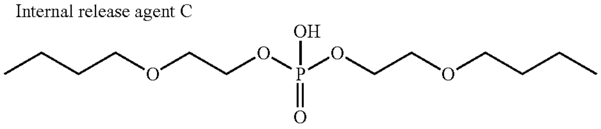

45 wt %

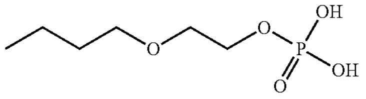

52 wt %

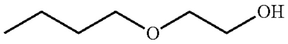

2 wt %

Internal release agent D

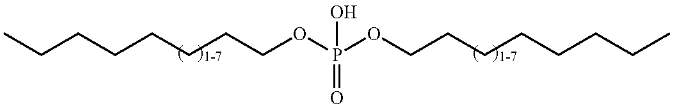

42 wt %

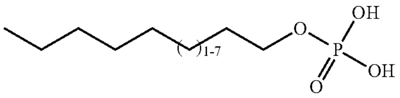

54 wt %

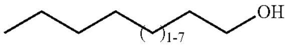

4 wt %

Example 7

A molded product (plastic lens) was produced in the same manner as in Example 1 except that the internal release agent A (1000 ppm) and the internal release agent D (500 ppm) were used instead of the phosphodiester (100), and releasability and transparency were confirmed. The results are shown in Table 3.

TABLE 3

| | | Addition amount (ppm) of internal release agent A | | | | | | |
|---|---|---|---|---|---|---|---|---|
| | | 0 (0) | 30 (4.8) | 50 (8) | 100 (16) | 500 (80) | 1,000 (160) | 5,000 (800) |
| Example 6 | Releasability | D | D | C | B | B | A | A |
| | Transparency | — | — | B | B | B | B | B |
| | | Addition amount (ppm) of internal release agent B | | | | | | |
| | | 0 (0) | 30 (29.7) | 50 (49.5) | 100 (99) | 500 (495) | 1,000 (990) | 5,000 (4950) |
| Comparative Example 1 | Releasability | D | D | D | C | B | A | A |
| | Transparency | — | — | — | B | B | B | C |
| | | Addition amount (ppm) of internal release agent C | | | | | | |
| | | 0 (0) | 30 (13.8) | 50 (23) | 100 (46) | 500 (230) | 1,000 (460) | 5,000 (2300) |
| Comparative Example 2 | Releasability | D | D | D | C | B | A | A |
| | Transparency | — | — | — | B | B | B | C |
| | | Addition amount (ppm) of internal release agent D | | | | | | |
| | | 0 (0) | 30 (12.6) | 50 (21) | 100 (42) | 500 (210) | 1,000 (420) | 5,000 (2100) |
| Comparative Example 3 | Releasability | D | D | D | D | B | A | A |
| | Transparency | — | — | — | — | B | B | D |
| | | Addition amount (ppm) of internal release agents A and D 1,500 | | | | | | |
| Example 7 | Releasability | B | | | | | | |
| | Transparency | B | | | | | | |

* amount in parentheses shows amount (ppm) of phosphodiester

Production Example 6

At room temperature, the internal release agent A obtained in Production Example 5 was neutralized (PH 7.3) with 28% by weight sodium methoxide, and the methanol mixed therein was removed under reduced pressure, whereby an internal release agent A-Na including a compound in the following composition ratio was obtained.

Internal release agent A-Na

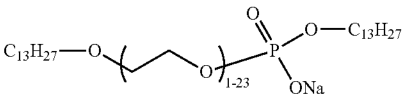

17 wt %

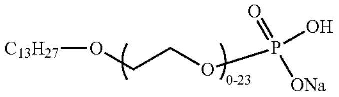

17 wt %

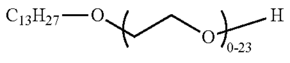

66 wt %

Example 8

A molded product (plastic lens) was produced in the same manner as in Example 6 except that the internal release agent A-Na was used instead of the internal release agent A, and releasability and transparency were confirmed. The results are shown in Table 4.

Example 9

A molded product (plastic lens) was produced in the same manner as in Example 6 except that the internal release agent A-Amine including a compound in the following composition ratio was used instead of the internal release agent A, and releasability and transparency were confirmed. The results are shown in Table 4.

Internal release agent A-Amine

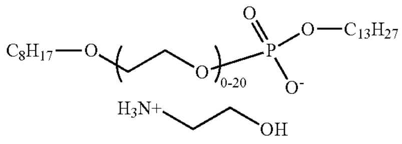

25 wt %

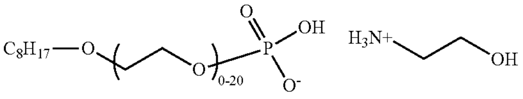

24 wt %

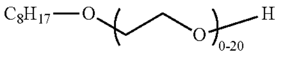

51 wt %

Production Example 7

At room temperature, the internal release agent B used in Comparative Example 1 was neutralized (PH 7.5) with 28% by weight sodium methoxide, and the methanol mixed therein was removed under reduced pressure, whereby an internal release agent B—Na including a compound in the following composition ratio was obtained.

Internal release agent B-Na

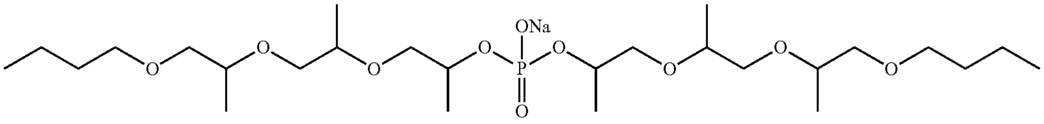

99 wt %

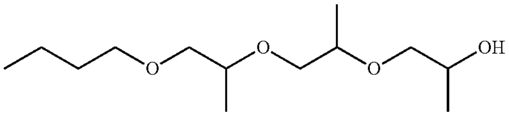

1 wt %

Comparative Example 4

A molded product (plastic lens) was produced in the same manner as in Example 6 except that the internal release agent B—Na was used instead of the internal release agent A, and releasability and transparency were confirmed. The results are shown in Table 4.

TABLE 4

| | | Addition amount (ppm) of internal release agent A-Na | | | | | | |
|---|---|---|---|---|---|---|---|---|
| | | 0 (0) | 30 (5.1) | 50 (8.5) | 100 (17) | 500 (85) | 1,000 (170) | 5,000 (850) |
| Example 8 | Releasability | D | C | B | B | B | A | A |
| | Transparency | — | B | B | B | B | B | B |

TABLE 4-continued

| | | Addition amount (ppm) of internal release agent A-Amine | | | | | | |
|---|---|---|---|---|---|---|---|---|
| | | 0 (0) | 30 (7.5) | 50 (12.5) | 100 (25) | 500 (125) | 1,000 (250) | 5,000 (1250) |
| Example 9 | Releasability | D | C | C | B | B | A | A |
| | Transparency | — | B | B | B | B | B | C |

| | | Addition amount (ppm) of internal release agent B-Na | | | | | | |
|---|---|---|---|---|---|---|---|---|
| | | 0 (0) | 30 (29.7) | 50 (49.5) | 100 (99) | 500 (495) | 1,000 (990) | 5,000 (4950) |
| Comparative Example 4 | Releasability | D | D | C | B | B | A | A |
| | Transparency | — | — | B | B | B | B | C |

* amount in parentheses shows amount (ppm) of phosphodiester

Example 10

The internal release agent A was put into each 100 ml sample bottle varying the addition amount within a range of 0 to 0.1 parts by weight (0 to 5,000 ppm), then, 0.3 parts by weight (15,000 ppm) of 2-(2'-hydroxy-5'-t-octylphenyl)benzotriazole (BIOSORB 583, manufactured by KYODO CHEMICAL CO., LTD.) as a UV absorber, 0.01 parts by weight (500 ppm) of dibutyl tin(II) dichloride as a catalyst, and 10.12 parts by weight of 2,5(6)-bis(isocyanatomethyl) bicyclo-[2.2.1]-heptane as a polymerization reactive compound were added thereto, and the solution was mixed by stirring at 20° C., whereby 7 homogeneous solutions in total were obtained. To the seven types of homogeneous solutions, 4.78 parts by weight of pentaerythritol tetrakis(3-mercaptopropionate) as a polymerization reactive compound and 5.1 parts by weight of 4-mercaptomethyl-1,8-dimercapto-3,6-dithiaoctane further were added, and the resulting product was mixed by stirring at 20° C., whereby seven types of homogeneous compositions in total were obtained. After degassing these compositions under reduced pressure of 0.13 kPa for 30 minutes, filtration was performed using a 1 μm PTFE filter, and these compositions were poured into a cavity (curve shape: 4 curves for both concave and convex surfaces, center thickness: 2 mm) in the mold composed of a glass mold and tape, and sealed with tape. These were put into a polymerization oven, then, slowly heated from 25° C. to 120° C. over a period of 19 hours, and held at 120° C. for 2 hours so as to polymerize these. After cooling, the glass mold and the tape were peeled off, and a molded product (plastic lens) comprised of a curable resin formed inside of the mold was taken out. The obtained molded product (plastic lens) was colorless and transparent, and had a refractive index ne of 1.60, an Abbe number νe of 40, and Tg of 114° C. The evaluation results of releasability and transparency are shown in Table 5.

Example 11

The internal release agent A was put into each 100 ml sample bottle varying the addition amount within a range of 0 to 0.1 parts by weight (0 to 5,000 ppm), then, 0.3 parts by weight (15,000 ppm) of 2-(2'-hydroxy-5'-t-octylphenyl)benzotriazole (BIOSORB 583, manufactured by KYODO CHEMICAL CO., LTD.) as a UV absorber, 0.01 parts by weight (500 ppm) of dibutyl tin(II) dichloride as a catalyst, and 10.12 parts by weight of m-xylylene diisocyanate as a polymerization reactive compound were added thereto, and the resulting product was mixed by stirring at 20° C., whereby seven types of homogeneous solutions in total were obtained. To each of these seven homogeneous solutions, 9.88 parts by weight of a mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane was further added as a polymerization reactive compound, and the resultant product was mixed by stirring at 20° C., whereby seven homogeneous compositions in total were obtained. After degassing the seven types of compositions under reduced pressure of 0.13 kPa for 30 minutes, filtration was performed using a 1 μm PTFE filter, and these compositions were poured into a cavity (curve shape: 4 curves for both concave and convex surfaces, center thickness: 2 mm) in the mold composed of a glass mold and tape, and sealed with tape. These were put into a polymerization oven, then, slowly heated from 25° C. to 120° C. over a period of 19 hours, and held at 120° C. for 2 hours so as to polymerize these. After cooling, the glass mold and the tape were peeled off, and a molded product (plastic lens) comprised of a curable resin formed inside was taken out. The obtained molded product (plastic lens) was colorless and transparent, and had a refractive index ne of 1.67, an Abbe number νe of 31, and Tg of 98° C. The evaluation results of releasability and transparency are shown in Table 5.

Example 12

Into seven sample bottles having 100 ml, 0.004 parts by weight of N,N-dimethylcyclohexylamine and 0.018 parts by weight of N,N-dicyclohexylmethylamine as catalysts, and 1.83 parts by weight of a mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane, as a polymerization reactive compound were added, respectively, and these were mixed by stirring at 20° C., whereby a homogeneous solution (1) was obtained. The internal release agent A was put into seven bottles having 100 ml varying the addition amount within a range of 0 to 0.1 parts by weight (0 to 5,000 ppm) as shown in Table 5, then, 0.2 parts by weight (10,000 ppm) of 2-(2-hydroxy-5-t-butylphenyl)-2H-benzotriazole (manufactured by BASF Corp., product name Tinuvin PS) as a UV absorber and 18.17 parts by weight of bis(2,3-epithiopropyl)disulfide as a polymerization reactive compound were added thereto, respectively, and these were mixed by stirring at 20° C., whereby seven types of homogeneous solution (2) were obtained. The homogeneous solution (1) was added to these seven types of homogeneous solution (2), and these were stirred at 20° C., where by polymerizable compositions were obtained. After degassing the seven types of polymerizable compositions under reduced pressure of 0.13 kPa for 30 minutes, filtration was performed using a 1 μm PTFE filter, and the polymerizable compositions were poured into a cavity (curve shape: 4 curves for both concave and convex surfaces, center thickness: 2 mm) in the mold composed of a glass mold and tape, and sealed with tape. These were put into a polymerization oven, then, slowly heated from 30° C. to 80° C. over a period of 19 hours, and held at 80° C. for 2 hours so as to polymerize these. After cooling, the glass mold and the tape were peeled off, and a molded product (plastic lens) comprised of a curable resin formed inside was taken out. The obtained molded product (plastic lens) was colorless and transparent, and had a refractive index ne of 1.74, an Abbe number νe of 32, and Tg of 78° C. The evaluation results of releasability and transparency are shown in Table 5.

Example 13

The internal release agent A was put into seven bottles having 100 ml varying the addition amount within a range of 0 to 0.1 parts by weight (0 to 5,000 ppm) as shown in Table 5, then, 0.3 parts by weight (15,000 ppm) of tetrabutylphosphonium bromide as a catalyst and 7.0 parts by weight of a mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane as a polymerization reactive compound were added thereto, respectively, and the resulting product was mixed by stirring at 40° C., whereby seven types of homogeneous solution were obtained. To these homogeneous solutions, 0.2 parts by weight (10,000 ppm) of product Tinuvin 384-2 manufactured by BASF Corp. as a UV absorber and 13.0 parts by weight of bisphenol A diglycidyl ether as a polymerization reactive compound were added, and the resulting product was mixed by stirring at 40° C., whereby seven types of homogeneous polymerizable compositions were obtained. After degassing these polymerizable compositions under reduced pressure of 0.13 kPa for 30 minutes, filtration was performed using a 1 μm PTFE filter, and the polymerizable compositions were poured into a cavity (curve shape: 4 curves for both concave and convex surfaces, center thickness: 2 mm) in the mold composed of a glass mold and tape, and sealed with tape. These were put into a polymerization oven, then, slowly heated from 70° C. to 120° C. over a period of 9 hours, and held at 120° C. for 6 hours so as to polymerize these. After cooling, the glass mold and the tape were peeled off, and a molded product (plastic lens) comprised of a curable resin formed inside was taken out. The obtained molded product (plastic lens) was colorless and transparent, and had a refractive index ne of 1.64, an Abbe number νe of 35, and Tg of 64° C. The evaluation results of releasability and transparency are shown in Table 5.

Example 14

The internal release agent A was put into each 100 ml sample bottle varying the addition amount within a range of 0 to 0.1 parts by weight (0 to 5,000 ppm) as shown in Table 5, then, 0.01 parts by weight (500 ppm) of 2-hydroxy-4-methylbenzophenone as a UV absorber, 0.6 parts by weight (30,000 ppm) of 1,1-di(t-hexylperoxy)cyclohexane as a polymerization initiator, and 20.0 parts by weight of diethylene glycol bis(allylcarbonate) as a polymerization reactive compound were added thereto, and the resulting product was mixed by stirring at 20° C., whereby seven types of polymerizable composition were obtained. After degassing the seven types of polymerizable compositions under reduced pressure of 0.13 kPa for 30 minutes, filtration was performed using a 1 μm PTFE filter, and the polymerizable compositions were poured into a cavity (curve shape: 4 curves for both concave and convex surfaces, center thickness: 2 mm) in the mold composed of a glass mold and tape, and sealed with tape. These were put into a polymerization oven, then, slowly heated from 75° C. to 130° C. over a period of 20 hours, and held at 130° C. for 3 hours so as to polymerize these. After cooling, the glass mold and the tape were peeled off, and a molded product (plastic lens) comprised of a curable resin formed inside was taken out. The obtained molded product (plastic lens) was colorless and transparent, and had a refractive index ne of 1.50 and an Abbe number νe of 58. The evaluation results of releasability and transparency are shown in Table 5.

Example 15

The internal release agent A was put into each 100 ml sample bottle varying the addition amount within a range of 0 to 0.1 parts by weight (0 to 5,000 ppm) as shown in Table 5, then, 0.01 parts by weight (500 ppm) of 2-hydroxy-4-methylbenzophenone as a UV absorber, 0.6 parts by weight (30,000 ppm) of 1,1-di(t-hexylperoxy)cyclohexane as a polymerization initiator, and 5.0 parts by weight of divinylbenzene and 15.0 parts by weight of ethoxybisphenol A diacrylate (NK ester A-BPE-10 (manufactured by Shin-Nakamura Chemical Co.)) as polymerization reactive compounds were added thereto, and the resulting product was mixed by stirring at 20° C., whereby seven types of homogeneous polymerizable compositions were obtained. After degassing these polymerizable compositions under reduced pressure of 0.13 kPa for 30 minutes, filtration was performed using a 1 μm PTFE filter, and the polymerizable compositions were poured into a cavity (curve shape: 4 curves for both concave and convex surfaces, center thickness: 2 mm) in the mold composed of a glass mold and tape, and sealed with tape. These were put into a polymerization oven, then, slowly heated from 75° C. to 130° C. over a period of 20 hours, and held at 130° C. for 3 hours so as to polymerize these. After cooling, the glass mold and the tape were peeled off, and a molded product (plastic lens) comprised of a curable resin formed inside was taken out. The obtained molded product (plastic lens) was colorless and transparent, and had a refractive index ne of 1.56 and an Abbe number νe of 38. The evaluation results of releasability and transparency are shown in Table 5.

TABLE 5

| | | Addition amount (ppm) of internal release agent A | | | | | | |
|---|---|---|---|---|---|---|---|---|
| | | 0 (0) | 30 (4.8) | 50 (8) | 100 (16) | 500 (80) | 1,000 (160) | 5,000 (800) |
| Example 10 | Releasability | D | C | B | B | A | A | A |
| | Transparency | — | B | B | B | B | B | D |

TABLE 5-continued

| | | Addition amount (ppm) of internal release agent A | | | | | | |
|---|---|---|---|---|---|---|---|---|
| | | 0 (0) | 30 (4.8) | 50 (8) | 100 (16) | 500 (80) | 1,000 (160) | 5,000 (800) |
| Example 11 | Releasability | D | C | B | B | B | A | A |
| | Transparency | — | B | B | B | B | B | D |
| Example 12 | Releasability | B | A | A | A | A | A | A |
| | Transparency | B | B | B | D | D | D | D |
| Example 13 | Releasability | D | D | D | D | D | B | A |
| | Transparency | — | — | — | — | — | B | B |
| Example 14 | Releasability | B | A | A | A | A | A | A |
| | Transparency | B | B | B | B | C | D | D |
| Example 15 | Releasability | B | A | A | A | A | A | A |
| | Transparency | B | B | B | B | C | D | D |

* amount in parentheses shows amount (ppm) of phosphodiester

Example 16

0.02 parts by weight of the internal release agent A, 0.3 parts by weight (15,000 ppm) of 2-(2'-hydroxy-5'-t-octylphenyl)benzotriazole (manufactured by KYODO CHEMICAL CO., LTD., product name BIOSORB 583) as a UV absorber, 0.008 parts by weight (400 ppm) of dimethyl tin(II) dichloride as a catalyst, 5.84 parts by weight of 2,5(6)-bis(isocyanatomethyl)bicyclo-[2.2.1]-heptane as a polymerization reactive compound, and 3.89 parts by weight of hexamethylene diisocyanate as polymerization reactive compound were added to a 100 ml sample bottle, and the resulting product was mixed by stirring at 20° C., whereby a homogeneous solution was obtained. 4.70 parts by weight of pentaerythritol tetrakis(3-mercaptopropionate) and 5.57 parts by weight of 4-mercaptomethyl-1,8-dimercapto-3,6-dithiaoctane further were further added thereto as a polymerization reactive compound, and the resulting product was mixed by stirring at 20° C., whereby a homogeneous composition in total were obtained. After degassing these compositions under reduced pressure of 0.13 kPa for 30 minutes, filtration was performed using a 1 μm PTFE filter, and these compositions were poured into a cavity (curve shape: 4 curves for both concave and convex surfaces, center thickness: 2 mm) in the mold composed of a glass mold and tape, and sealed with tape. These were put into a polymerization oven, then, slowly heated from 25° C. to 120° C. over a period of 15 hours, and held at 120° C. for 4 hours so as to polymerize these. After cooling, the glass mold and the tape were peeled off, and a molded product (plastic lens) comprised of a curable resin formed inside was taken out. The obtained molded product (plastic lens) was colorless and transparent, and had a refractive index ne of 1.60, an Abbe number νe of 39, and Tg of 92° C. The evaluation results of releasability and transparency are shown in Table 6.

Example 17

0.10 parts by weight of the internal release agent A, 1.5 parts by weight of viosorb 583 (ultraviolet absorber: registered trademark, manufactured by KYODO CHEMICAL CO., LTD.), 0.028 parts by weight of N-benzyl-2-methylimidazole, and 23.9 parts by weight of 1,5-pentamethylene diisocyanate were mixed, and after the resulting product was stirred and dissolved at room temperature for 15 minutes, and 27.9 parts by weight of 1,5-pentamethylene diisocyanate modified composition was mixed therewith, whereby polyisocyanate liquid was produced. The isocyanurate mononuclear body concentration of this polyisocyanate solution was 35%. 29.1 parts by weight of polythiol including 4,8- and 4,7- and 5,7-dimercaptomethyl-1,11-dimercapto-3,6,9-trithiaundecane as a main component and 19.1 parts by weight of pentaerythritol tetrakis(3-mercaptopropionate) were added thereto, and the resulting product was mixed by stirring at room temperature, a homogeneous solution of a monomer mixture was obtained. The viscosity of the homogeneous solution was 40 mPa·s. This homogeneous solution was subjected to degassing at room temperature, under reduced pressure for 30 minutes, then, filtration was performed using a 1 μm TEFLON (registered trademark) filter, and homogeneous solution was injected into a mold (curve shape: 4 curves for both concave and convex surfaces, center thickness: 2 mm) formed of a glass mold and tape, and sealed with tape. This was put into an oven, and slowly heated from 25° C. to 120° C. for 24 hours so as to polymerize this. After the polymerization ended, the mold was taken out from the oven, then, the product was released from the mold, and annealing was performed at 120° C. for 2 hours, whereby a resin molded product was obtained. The resin molded product was colorless and transparent, and had a refractive index (ne) of 1.60, an Abbe number (νe) of 39, and heat resistance of 89° C. The evaluation results of releasability and transparency are shown in Table 6.

Example 18

0.1 part by weight (1,000 ppm) of the internal release agent A, 1.5 parts by weight (15,000 ppm) of 2-(2'-hydroxy-5'-t-octylphenyl)benzotriazole (manufactured by KYODO CHEMICAL CO., LTD., product name viosorb 583) as a UV absorber, and 58.9 parts by weight of bis(4-isocyanatocyclohexyl)methane were mixed by stirring at 20° C., whereby a homogeneous solution was obtained. 41.1 parts by weight of a mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane, and 0.15 parts by weight (1500 ppm) of dibutyl tin(II) dichloride were added to the homogeneous solution, and the resultant product was mixed by stirring at 20° C., whereby a mixed solution was obtained. The mixed solution was degassed at 600 Pa for 1 hour, then, filtered using a PTFE filter having a pore size of 1 μm, and injected into a planar glass mold of 4 C having a center thickness of 2 mm and a diameter of 80 mm. The mold was put into a polymerization oven, and slowly heated from 20° C. to 130° C. for a period of 21 hours so as to polymerize. After the polymerization ended, the mold die was taken out from the oven. The obtained plastic lens was further subjected to an annealing treatment at 130° C. for 2 hours. The obtained planar lens having a thickness of 2 mm was transparent, and had a refractive index (ne) of 1.60, an Abbe number (νe) of 39, and heat resistance of 136° C., which indicated that the composition was suitable as a transparent resin for optical materials. The evaluation results of releasability and transparency are shown in Table 6.

Example 19

0.10 parts by weight of the internal release agent A, 0.20 parts by weight of dimethyl tin dichloride (manufactured by Honjo Chemical Corporation, product name: Nestin P), 1.50 parts by weight of 2-(2-hydroxy-5-tert-octylphenyl)-2H-benzotriazole (manufactured by Sakai Chemical Industry Co., Ltd., product name Viosorb 583), and 53.0 parts by weight of isophorone diisocyanate were mixed by stirring. Thereafter, 47.0 parts by weight of a mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane was mixed therein, whereby a composition was produced. The obtained polymerization law material was filtered using a 1.0 μm TEFLON (registered trademark) filter, and degassed in vacuum of 400 Pa or less for 60 minutes. The degassed composition was injected into a mold formed of a planar glass mold of 4 C having a center thickness of 2 mm and a diameter of 80 mm and tape. Thereafter, polymerization was performed in a heating furnace at 25° C. to 120° C. for 20 hours, and after being cooled, the glass mold and the tape were removed, whereby a thiourethane molded product was obtained. Annealing was further performed at 130° C. for 2 hours. The obtained planar lens having a thickness of 2 mm was transparent, and had a refractive index (ne) of 1.60, an Abbe number (νe) of 38, and heat resistance of 130° C., which indicated that the composition was suitable as a transparent resin for optical materials. The evaluation results of releasability and transparency are shown in Table 6.

Example 20

0.10 parts by weight of the internal release agent A, 0.17 parts by weight of dibutyl tin(II) dichloride, 1.50 parts by weight of 2-(2-hydroxy-5-tert-octylphenyl)-2H-benzotriazole (manufactured by Sakai Chemical Industry Co., Ltd., product name Viosorb 583), 23.2 parts by weight of isophorone diisocyanate, and 19.8 parts by weight of hexamethylene diisocyanate were mixed by stirring. Thereafter, 57.0 parts by weight of pentaerythritol tetrakis(3-mercaptopropionate) was added thereto, whereby a composition was produced. The obtained polymerization law material was filtered using a 1.0 μm TEFLON (registered trademark) filter, and degassed in vacuum of 400 Pa or less for 60 minutes. The degassed composition was injected into a mold formed of a planar glass mold of 4 C having a center thickness of 2 mm and a diameter of 80 mm and tape. Thereafter, polymerization was performed in a heating furnace at 35° C. to 130° C. for 21 hours, and after being cooled, the glass mold and the tape were removed, whereby a thiourethane molded product was obtained. Annealing was further performed at 130° C. for 2 hours. The obtained planar lens having a thickness of 2 mm was transparent, and had a refractive index (ne) of 1.56, an Abbe number (νe) of 41, and heat resistance of 82° C., which indicated that the composition was suitable as a transparent resin for optical materials. The evaluation results of releasability and transparency are shown in Table 6.

Example 21

0.1 part by weight (1,000 ppm) of the internal release agent A, 2.0 parts by weight (20,000 ppm) of 2-(2'-hydroxy-5'-t-octylphenyl)benzotriazole (manufactured by KYODO CHEMICAL CO., LTD., product name viosorb 583) as a UV absorber, 27.6 parts by weight of bis(4-isocyanatocyclohexyl)methane, and 27.6 parts by weight of isophorone diisocyanate were mixed by stirring at 20° C., whereby a homogeneous solution was obtained. 44.8 parts by weight of a mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane, and 0.17 parts by weight (1700 ppm) of dimethyl tin(II) dichloride were added to the homogeneous solution, and the resultant product was mixed by stirring at 20° C., whereby a mixed solution was obtained. The mixed solution was degassed at 600 Pa for 1 hour, then, filtered using a PTFE filter having a pore size of 1 μm, and injected into a planar a glass mold of 4 C having a center thickness of 2 mm and a diameter of 80 mm. The mold die was put into a polymerization oven, and slowly heated from 20° C. to 130° C. for 21 hours so as to polymerize the solution. After the polymerization ended, the mold die was taken out from the oven. The obtained planar lens was further subjected to an annealing treatment at 130° C. for 2 hours. The obtained planar lens having a thickness of 2 mm was transparent, and had a refractive index (ne) of 1.60, an Abbe number (νe) of 38, and heat resistance of 117° C., which indicated that the composition was suitable as a transparent resin for optical materials. The evaluation results of releasability and transparency are shown in Table 6.

Example 22

1.0 part by weight (10,000 ppm) of the internal release agent A, 58.8 parts by weight of a propylene oxide adduct of trimethylolpropane (manufactured by Bayer AG; Desmophen 4011T), and 0.40 parts by weight (4,000 ppm) of TINUVIN 292 (manufactured by BASF Corp; light stabilizer) were mixed together and dissolved, whereby a homogeneous solution was obtained. 41.2 parts by weight of a mixture of 2,4-tolylene diisocyanate and 2,6-tolylene diisocyanate and 1.50 parts by weight (15,000 ppm) of a benzotriazole-based compound (Viosorb 583 (2-(2'-hydroxy-5'-tert-octylphenyl)benzotriazole)) were mixed together and dissolved, whereby a homogeneous solution was obtained. After mixing the respective solutions at 20° C. and degassing at 400 Pa, the resulting solution was injected into a planar mold of 4 C having a diameter of 80 mm. This was put into a polymerization oven, and slowly heated from 15° C. to 120° C. for 24 hours so as to polymerize this. After the polymerization ended, the mold was taken out from the oven, and release work from the mold was performed. The releasability was good and peeling of the mold was not observed. The obtained molded product was further subjected to an annealing treatment at 120° C. for 2 hours. The obtained molded product was transparent, and had no striae observed, and the refractive index (ne) thereof was 1.54, Tg was 81° C., which indicated that the molded product was suitable for optical material applications. The evaluation results of releasability and transparency are shown in Table 6.

TABLE 6

| | | Addition amount (ppm) of internal release agent A |
|---|---|---|
| | | 1,000 (160) |
| Example 16 | Releasability | B |
| | Transparency | B |
| Example 17 | Releasability | B |
| | Transparency | B |
| Example 18 | Releasability | A |
| | Transparency | B |
| Example 19 | Releasability | B |
| | Transparency | B |
| Example 20 | Releasability | B |
| | Transparency | B |
| Example 21 | Releasability | A |
| | Transparency | B |
| | | 10,000 (1,600) |
| Example 22 | Releasability | A |
| | Transparency | B |

* amount in parentheses shows amount (ppm) of phosphodiester

This application claims priority from Japanese Patent Application No. 2014-265858 filed on Dec. 26, 2014, the content of which is incorporated herein by reference in its entirety.

The invention claimed is:

1. A composition, comprising:

a polymerization reactive compound; and an internal release agent containing at least one phosphodiester compound represented by the following general formula (1):

(1)

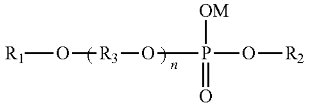

wherein, in the formula, $R_1$ and $R_2$ independently represent a hydrocarbon group having 1 to 30 carbon atoms, which is optionally substituted with at least one hydroxyl group; $R_3$ represents an alkylene group having 2 to 4 carbon atoms and a plurality of $R_3$'s may be the same as or different from each other; M represents a hydrogen atom, an ammonium ion, an alkali metal ion, or a monovalent/divalent alkali earth metal ion; and n is an integer of 1 to 60.

2. The composition according to claim 1, wherein the amount of the phosphodiester compound represented by the general formula (1) is $1\times10^{-1}$ to $5\times10^{4}$ ppm with respect to the polymerization reactive compound.

3. The composition according to claim 1, wherein the polymerization reactive compound is at least one kind of compound selected from the group consisting of a polyiso(thio)cyanate compound, a poly (thio)epoxy compound, a polyoxetanyl compound, a polythietanyl compound, a poly(meth)acryloyl compound, a polyalkene compound, an alkyne compound, a poly(thi)ol compound, a polyamine compound, an acid anhydride, and a polycarboxylic acid compound.

4. A molded product obtained by polymerizing the composition according to claim 1.

5. An optical material comprised of the molded product according claim 4.

6. A plastic lens comprised of the molded product according to claim 4.

7. A process for producing a plastic lens, comprising:

a step of cast-polymerizing the composition according to claim 1.

8. A plastic lens obtained by the production method according to claim 7.

9. An optical material comprising an internal release agent containing at least one phosphodiester compound represented by the following general formula (1):

(1)

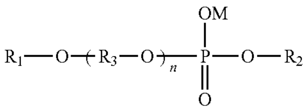

wherein, in the formula, $R_1$ and $R_2$ independently represent a hydrocarbon group having 1 to 30 carbon atoms, which is optionally substituted with at least one hydroxyl group; $R_3$ represents an alkylene group having 2 to 4 carbon atoms and a plurality of $R_3$'s may be the same as or different from each other; M represents a hydrogen atom, an ammonium ion, an alkali metal ion, or a monovalent/divalent alkali earth metal ion; and n is an integer of 1 to 60.

10. A plastic lens comprising an internal release agent containing at least one phosphodiester compound represented by the following general formula (1):

(1)

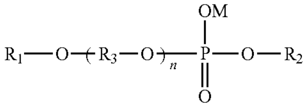

wherein, in the formula, $R_1$ and $R_2$ independently represent a hydrocarbon group having 1 to 30 carbon atoms, which is optionally substituted with at least one hydroxyl group; $R_3$ represents an alkylene group having 2 to 4 carbon atoms and a plurality of $R_3$'s may be the same as or different from each other; M represents a hydrogen atom, an ammonium ion, an alkali metal ion, or a monovalent/divalent alkali earth metal ion; and n is an integer of 1 to 60.

* * * * *